United States Patent [19]

Yamakawa et al.

[11] Patent Number: 5,672,714
[45] Date of Patent: Sep. 30, 1997

[54] METHOD OF MANUFACTURING A 3-SUBSTITUTED-3-OXO-2-HALOPROPIONIC ACID AMIDE COMPOUND AND METHOD OF MANUFACTURING A 3-SUBSTITUTED-3-OXO-2-(5,5-DIMETHYLHYDANTOIN-3-YL) PROPIONIC ACID AMIDE COMPOUND

[75] Inventors: Katsuyoshi Yamakawa; Tadahisa Sato, both of Minami-ashigara, Japan

[73] Assignee: Fuji Photo Film Co., Ltd., Kanagawa-ken, Japan

[21] Appl. No.: 555,062

[22] Filed: Nov. 8, 1995

[30] Foreign Application Priority Data

Nov. 14, 1994 [JP] Japan ................. 6-302681

[51] Int. Cl.$^6$ ................. C07D 233/40
[52] U.S. Cl. ................. 548/319.5; 548/312.1
[58] Field of Search ................. 548/319.5, 312.1

[56] References Cited

U.S. PATENT DOCUMENTS

| | | | |
|---|---|---|---|
| 3,960,570 | 6/1976 | Oishi et al. | 96/100 |
| 5,066,574 | 11/1991 | Kubota et al. | 430/557 |
| 5,183,731 | 2/1993 | Takahashi et al. | 430/551 |
| 5,399,474 | 3/1995 | Tomotake et al. | 96/100 |

FOREIGN PATENT DOCUMENTS

| | | |
|---|---|---|
| 307242 | 5/1993 | Japan . |
| 611808 | 6/1994 | Japan . |
| 619084 | 6/1994 | Japan . |

*Primary Examiner*—Joseph McKane
*Assistant Examiner*—Richard S. Myers, Jr.
*Attorney, Agent, or Firm*—Birch, Stewart, Kolasch & Birch, LLP

[57] ABSTRACT

There is disclosed a method of manufacturing a 3-substituted-3-oxo-2-halopropionic acid amide compound, comprising halogenating a 3-substituted-3-oxopropionic acid amide compound with a 1,3-dihalo-5,5-dimethylhydantoin. There is also disclosed a method of manufacturing a 3-substituted-3-oxo-2-(5,5-dimethylhydantoin-3-yl)propionic acid amide compound, comprising steps of halogenating a 3-substituted-3-oxopropionic acid amide compound with a 1,3-dihalo-5,5-dimethylhydantoin, to obtain a corresponding 3-substituted-3-oxo-2-halopropionic acid amid compound, and reacting the resultant amide compound with 5,5-dimethylhydantoin in the presence of a base. This 3-substituted-3-oxo-2-hydantoinylpropionic acid amide compound is useful as a photographic yellow coupler for a color-photographic light-sensitive material.

27 Claims, No Drawings

METHOD OF MANUFACTURING A 3-SUBSTITUTED-3-OXO-2-HALOPROPIONIC ACID AMIDE COMPOUND AND METHOD OF MANUFACTURING A 3-SUBSTITUTED-3-OXO-2-(5,5-DIMETHYLHYDANTOIN-3-YL) PROPIONIC ACID AMIDE COMPOUND

FIELD OF THE INVENTION

The present invention relates to a yellow coupler for a silver halide color-photographic light-sensitive material. The present invention also relates to a silver halide color-photographic light-sensitive material containing the yellow coupler.

Further, the present invention relates to a novel method of manufacturing a yellow coupler to be used for a silver halide color-photographic light-sensitive material. The present invention also relates to a novel method of manufacturing a synthetic intermediate of the yellow coupler.

BACKGROUND OF THE INVENTION

In recent years, in silver halide color-photographic light-sensitive materials, in many cases, there is a tendency to use, in place of conventional four-equivalent couplers that require four atoms of silver to form one molecule of a dye, two-equivalent couplers, wherein a suitable substituent is introduced at the coupling position (active site) where the coupler reacts with the oxidation product of a developing agent, so that two atoms of silver are enough to form one molecule of a dye.

Among them, as yellow couplers for color photographic materials, pivaroylacetanilides, benzoylacetanilides, and malondiamides are generally used. From a viewpoint of saving silver, a so-called two-equivalent coupler, which splits off a releasable group, such as a 5-membered heterocyclic group, at a coupling reaction with an oxidation product of a developing agent, has been generally used.

Recently, a yellow coupler that splits off an inexpensively available 5,5-dimethylhydantoin as a releasable group has particularly attracted photographic chemists' attention because, for example, it provides a high coloring property in combination with the oxidation product of a developing agent (JP-A ("JP-A" means unexamined published Japanese Patent Application) Nos. 11808/1994, 19084/1994, and 307242/1993, and U.S. Pat. No. 5,399,474). Its preparation method contains the steps illustrated below:

A four-equivalent coupler represented by formula (VI) (i.e. a 3-substituted-3-oxopropionic acid amide compound) is halogenized (e.g. chlorinated with sulfuryl chloride), to obtain a 3-substituted-3-oxo-2-halopropionic acid amide compound (i.e. a compound represented by formula (IV)), followed by a substitution reaction with 5,5-dimethylhydantoin, whereby a two-equivalent coupler (i.e. a compound represented by formula (V)) is obtained.

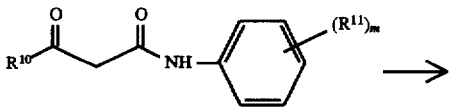

general formula (VI)

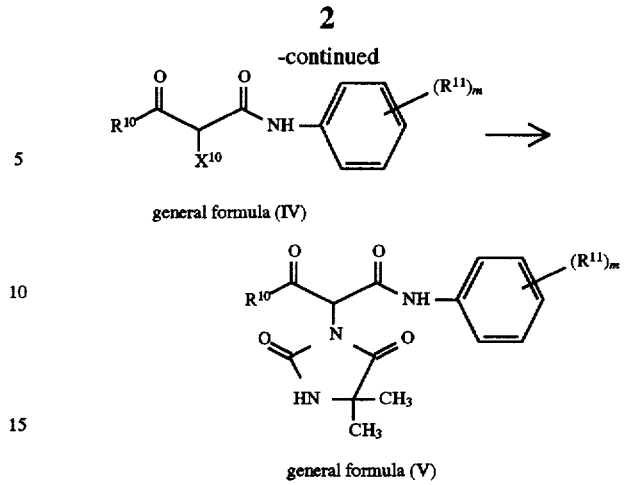

general formula (IV)

general formula (V)

wherein $R^{10}$ represents an alkyl group or an aryl group, $R^{11}$ represents a substituent, $X^{10}$ represent a halogen atom, and m represent an integer ranging from 0 to 5.

This preparation method is a general method that can be applied to prepare a two-equivalent coupler that splits off another type of 5-membered heterocyclic ring. However, when a halogenating agent, such as chlorine, sulfuryl chloride, and bromine, is used according to this method, sometimes halogenation occurs not only at the position of an active methylene group but also at another portion of the molecule (e.g. at a benzene ring of the anilide group and at a substituent $R^{11}$ on the ring [for example, the case in which $R^{11}$ has a carbon-carbon double bond or an aromatic ring]). Moreover, when these halogenating agents are used, a hydrogen halide, such as hydrogen chloride and hydrogen bromide, is generated, which results in some problems. For example, when a cyclopropane ring exists in a molecule, sometimes an open-ring occurs. Furthermore, since processing after a reaction necessitates neutralizing a reaction solution according to a separation of solutions, followed by a washing, the processing is troublesome. Further, halogenating agents high in reactivity are generally to be used with halogen-containing solvents. However, there is a tendency for the use of halogen-containing solvents to be severely restricted, to solve recent environmental problems. Therefore halogenating agents that do not require the use of a halogen-containing solvent are strongly demanded.

As a halogenating agent that does not generate a hydrogen halide, a compound such as N-chlorosuccinimide (NCS) and N-bromosuccinimide (NBS) can be used. However, these halogenating agents are not only expensive, they also produce succinimide. Therefore, the use of these halogenating agents necessitates an additional operation to remove succinimide by washing, and so on, prior to the next step (substitution reaction). In other words, succinimide, if not removed, would participate the substitution reaction at the next reaction.

As mentioned above, general known methods are each troublesome at the stage of post-processing, and they also increase cost, since a raw material is expensive. Moreover, these methods cause a side reaction, so that purity of the object is reduced. Therefore, the demand for improving the above problems is increasing. These days, the demand for reduction in the cost of a coupler has become much stronger than before. Therefore the development of technology to reduce the cost is strongly desired.

Further, these couplers, although excellent in color-forming properties, have such defects that the solubility, particularly in low-boiling-point solvents, is low; the dispersion stability is poor; and thus in using this coupler productivity is low and the cost is high, since the synthesis intermediates at the time of the production of the couplers exhibit low solubility in organic solvents. Therefore, improvements of these couplers are strongly desired.

SUMMARY OF THE INVENTION

An object of the present invention is to provide a method of manufacturing simply, at low cost and high purity, with a good yield, a yellow coupler for use in a silver halide color photographic light-sensitive material.

Another object of the present invention is to provide a method of manufacturing an intermediate of the yellow coupler.

A further object of the present invention is to provide a novel two-equivalent yellow coupler that can be produced inexpensively and that is excellent in color-forming properties.

A further object of the present invention is to provide a silver halide color photographic material containing the two-equivalent yellow coupler.

A still further object of the present invention is to provide a novel two-equivalent yellow coupler that is high in solubility in low-boiling-point and high-boiling-point solvents used for dispersing the coupler, and that exhibits an excellent dispersion stability in these solvents.

A still further object of the present invention is to provide a silver halide color photographic material containing the two-equivalent yellow coupler.

A still further object of the present invention is to provide a novel two-equivalent yellow coupler whose production can be made through its synthesis intermediate, which is high in solubility in organic solvents and which can produce the coupler with high productivity.

A still further object of the present invention is to provide a silver halide color photographic material containing the two-equivalent yellow coupler.

DETAILED DESCRIPTION OF THE INVENTION

The object of the present invention has been attained by the following methods. That is, the present invention provides:

(1) A method of manufacturing a 3-substituted-3-oxo-2-halopropionic acid amide compound represented by general formula (I):

general formula (I)

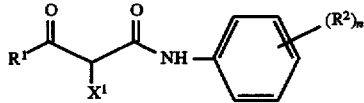

wherein $R^1$ represents an alkyl group, a cycloalkyl group, an aryl group, an amino group, or an indoline-1-yl group; $R^2$ represents a substituent; $X^1$ represents a halogen atom; and n represents an integer ranging from 0 to 5, with the proviso that when n is 2 or greater, the substituents represented by $R^2$ are the same or different, comprising using 1,3-dihalo-5,5-dimethylhydantoin;

(2) The method as described in (1), comprising halogenating a 3-substituted-3-oxopropionic acid amide compound with a 1,3-dihalo-5,5-dimethylhydantoin, to obtain the 3-substituted-3-oxo-2-halopropionic acid amide compound represented by general formula (I);

(3) The method as described in (1) or (2), wherein the 1,3-dihalo-5,5-dimethylhydantoin is 1,3-dibromo-5,5-dimethylhydantoin or 1,3-dichloro-5,5-dimethylhydantoin (hereinafter the manufacturing method stated in the above (1), (2), and (3) are referred to as fist invention of the present invention);

(4) A method of manufacturing a 3-substituted-3-oxo-2-(5,5-dimethylhydantoin-3-yl)propionic acid amide compound represented by general formula (II):

general formula (II)

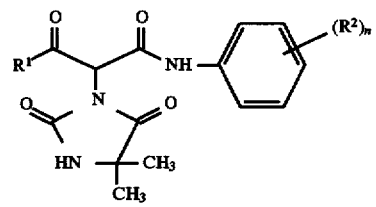

wherein $R^1$ represents an alkyl group, a cycloalkyl group, an aryl group, an amino group, or an indoline-1-yl group; $R^2$ represents a substituent; and n represents an integer ranging from 0 to 5, with the proviso that when n is 2 or greater, the substituents represented by $R^2$ are the same or different, comprising steps of halogenating a 3-substituted-3-oxopropionic acid amide compound with a 1,3-dihalo-5,5-dimethylhydantoin, to obtain a corresponding 3-substituted-3-oxo-2-halopropionic acid amid compound represented by general formula (I):

general formula (I)

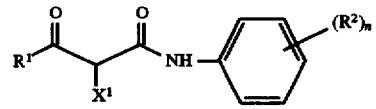

wherein $R^1$, $R^2$ and n each have the same meanings as those defined in general formula (II), and $X^1$ represents a halogen atom, and reacting the 3-substituted-3-oxo-2-halopropionic acid amide compound with 5,5-dimethylhydantoin in the presence of a base;

(5) The method as described in (4), wherein the 1,3-dihalo-5,5-dimethylhydantoin is 1,3-dibromo-5,5-dimethylhydantoin or 1,3-dichloro-5,5-dimethylhydantoin (hereinafter the manufacturing method stated in the above (4) and (5) are referred to as second invention of the present invention);

(6) A 3-substituted-3-oxo-2-hydantoinylpropionic acid amide compound represented by general formula (Y):

general formula (Y)

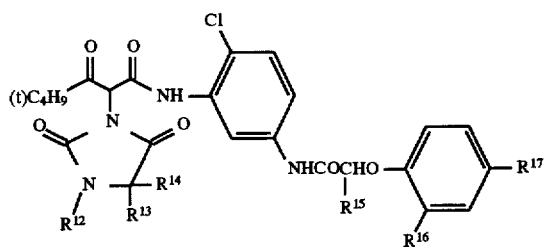

wherein $R^{12}$, $R^{13}$, and $R^{14}$ each represent a hydrogen atom or an alkyl group; $R^{15}$ represents an alkyl group having 3 or more carbon atoms; and $R^{16}$ and $R^{17}$ each represent a tertiary alkyl group having 4 or more carbon atoms (hereinafter the compound stated in the above (6) is referred to as third invention of the present invention);

(7) A photographic yellow coupler represented by general formula (Y):

general formula (Y)

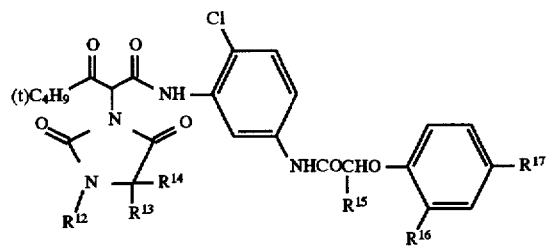

wherein $R^{12}$, $R^{13}$, and $R^{14}$ each represent a hydrogen atom or an alkyl group; $R^{15}$ represents an alkyl group having 3 or more carbon atoms; and $R^{16}$ and $R^{17}$ each represent a tertiary alkyl group having 4 or more carbon atoms (hereinafter the coupler stated in the above (7) is referred to as fourth invention of the present invention); and (8) A silver halide color-photographic light-sensitive material, containing a yellow coupler represented by general formula (Y):

general formula (Y)

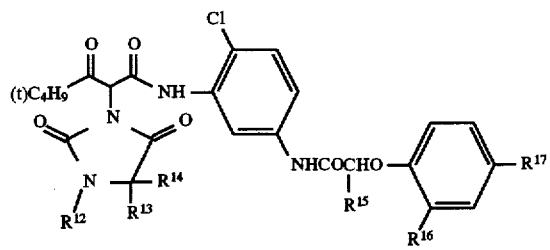

wherein $R^{12}$, $R^{13}$, and $R^{14}$ each represent a hydrogen atom or an alkyl group; $R^{15}$ represents an alkyl group having 3 or more carbon atoms; and $R^{16}$ and $R^{17}$ each represent a tertiary alkyl group having 4 or more carbon atoms, in at least one hydrophilic colloid layer on a support (hereinafter the light-sensitive material stated in the above (8) is referred to as fifth invention of the present invention).

In this specification, "the present invention" denotes all of the first, second, third, fourth, and fifth inventions, unless otherwise specified.

Further, "the manufacturing methods of the present invention" denote both the above first and second inventions, unless otherwise specified.

The manufacturing methods of the present invention are explained below in detail. The reaction scheme is illustrated as follows:

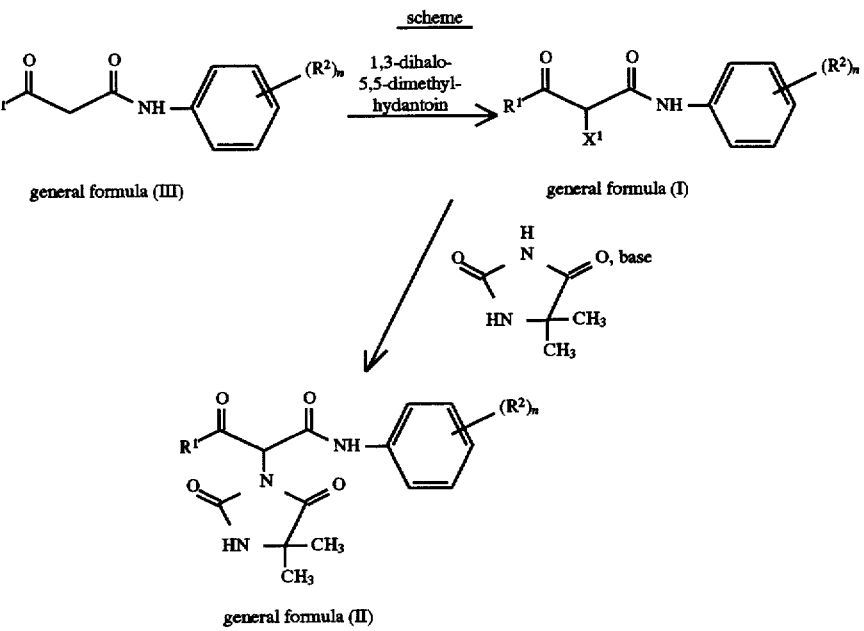

The compound represented by general formula (III) can be easily prepared by a condensation reaction of a 3-substituted-3-oxopropionic acid ester with anilines.

First, compounds are explained in detail.

In this specification, the alkyl group, the cycloalkyl group, the aryl group, and the amino group of $R^1$, according to the definition of each general formula, each mean substituted and unsubstituted groups, unless these groups are defined otherwise.

$R^1$ represents a substituted or unsubstituted alkyl group preferably having 1 to 18 carbon atoms (e.g. methyl, ethyl, tert-butyl, tert-octyl), a substituted or unsubstituted cycloalkyl group preferably having 3 to 18 carbon atoms (e.g. cyclopropyl, 1-ethylcyclopropyl, 1-benzylcyclopropyl, adamantyl), a substituted or unsubstituted aryl group preferably having 6 to 26 carbon atoms (e.g. phenyl, naphtyl), a substituted or unsubstituted amino group preferably having 0 to 26 carbon atoms (e.g. amino, N,N-dimethylamino, anilino), or an indoline-1-yl group.

The substituent may be any substituent known as a substituent for use in a photographic yellow coupler, and it includes a substituted or unsubstituted alkoxy group preferably having 1 to 18 carbon atoms (e.g. methoxy, octadecoxy), a substituted or unsubstituted alkyl group preferably having 1 to 18 carbon atoms (e.g. methyl, ethyl, propyl, octyl), a substituted or unsubstituted aryl group preferably having 6 to 26 carbon atoms (e.g. phenyl, naphthyl, 2-chloro-5-(1-dodecyloxycarbonylethoxycarbonyl)phenyl), a halogen atom (e.g. a fluorine atom, a chlorine atom), a cyano group, a nitro group, a substituted or unsubstituted alkylsufonyl group preferably having 1 to 18 carbon atoms (e.g. methanesulfonyl, butanesulfonyl, hexadecanesulfonyl), and a substituted or unsubstituted alkoxycarbonyl group preferably having 2 to 18 carbon atoms (e.g. methoxycarbonyl, ethoxycarbonyl).

More preferably, $R^1$ represents a tertiary alkyl group having 4 to 18, more preferably 4 to 8, carbon atoms (e.g. tert-butyl, tert-octyl); a cycloalkyl group that bonds with its tertiary carbon atom, preferably having 4 to 18, more preferably 4 to 10, carbon atoms (e.g. 1-methylcyclopropyl, 1-ethylcyclopropyl, 1-benzylcyclopropyl, adamantyl); a phenyl group that has an alkoxy group having 1 to 18 carbon atoms at its p-position; a substitutred anilino group having 6 to 26 carbon atoms (e.g. 2-chloro-5-(1-dodecyloxycarbonylethoxycarbonyl)phenylamino); or an indoline-1-yl group. Particularly preferably, $R^1$ represents a tert-butyl group, a 1-ethylcyclopropyl group, a p-methoxyphenyl group, or an indoline-1-yl group.

When $R^1$ represents a substituted anilino group, the compound represented by general formula (I) is preferably represented by general formula (VII):

general formula (VII)

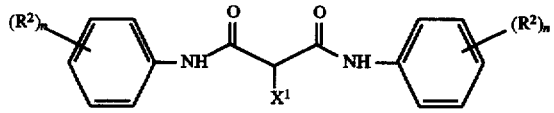

wherein $R^2$, $X^1$, and n each have the same meanings as those of general formula (I).

$R^2$ represents a substituent that is able to bond to the benzene ring, and it may be any substituent known as a substituent for use in a photographic yellow coupler. Examples of the substituent include a halogen atom (e.g. a fluorine atom, a chlorine atom, a bromine atom), a cyano group, a nitro group, an amino group, a hydroxyl group, a carboxyl group, a sulfo group, a substituted or unsubstituted alkoxy group preferably having 1 to 30 carbon atoms (e.g. methoxy, methoxyethoxy, octadecoxy), a substituted or unsubstituted alkoxycarbonyl group preferably having 2 to 30 carbon atoms (e.g. methoxycarbonyl, dodecoxycarbonyl, 1-dodecyloxycarbonyl-ethoxycarbonyl), a substituted or unsubstituted acylamino group preferably having 1 to 30 carbon atoms (e.g. acetylamino, palmitoylamino, stearoylamino, oleoylamino, 2-(2,4-di-tert-amylphenoxy) butanoylaminophthalimido), a substituted or unsubstituted sulfonamido group preferably having 1 to 30 carbon atoms (e.g. methanesulfonamido, hexadecanesulfonamido), a substituted or unsubstituted carbamoyl group preferably having 1 to 30 carbon atoms (e.g. carbamoyl, N,N-dimethylcarbamoyl), a substituted or unsubstituted sulfamoyl group preferably having 0 to 30 carbon atoms (e.g. N-phenylsulfamoyl, N-(2-chlorophenyl)sulfamoyl), a substituted or unsubstituted alkylsulfony group preferably having 1 to 30 carbon atoms (e.g. methanesulfonyl, butanesulfonyl), a substituted or unsubstituted acyl group preferably having 1 to 30 carbon atoms (e.g. formyl, acetyl, butanoyl, palmitoyl), a substituted or unsubstituted oxycarbonylamino group preferably having 2 to 30 carbon atoms (e.g. tert-butoxycarbonylamino, benzyloxycarbonylamino, phenoxycarbonylamino), or a substituted or unsubstituted imino group preferably having 1 to 30 carbon atoms (e.g. benzylideneamino).

More preferably, $R^2$ represents a halogen atom, a nitro group, an amino group, an alkoxy group preferably having 1 to 18 carbon atoms, an alkoxycarbonyl group preferably having 1 to 20 carbon atoms, an acylamino group preferably having 1 to 30 carbon atoms, or a substituted or unsubstituted sulfamoyl group preferably having 0 to 30 carbon atoms.

n represents an integer ranging from 0 to 5, preferably 1 to 3, and most preferably 2.

$X^1$ represents a halogen atom, with preferred examples being a chlorine atom and a bromine atom.

The combination of the substitution position and the substituent for $(R^2)_n$ as illustrated below are particularly preferred. A benzene ring of the anilide residue is shown below.

formula

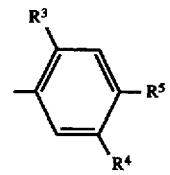

wherein $R^3$ represents a halogen atom, or a substituted or unsubstituted alkoxy group having 1 to 18 carbon atoms; $R^4$ represents a nitro group, an amino group, a substituted or unsubstituted alkoxycarbonyl group having 1 to 20 carbon atoms, a substituted or unsubstituted acylamino group having 1 to 30 carbon atoms, or a substituted or unsubstituted sulfamoyl group having 0 to 30 carbon atoms; and $R^5$ represents a hydrogen atom or a halogen atom.

The following combination is particularly preferred when $R^1$ represents a tert-butyl group: $R^3$ represents a halogen atom (most preferably a chlorine atom), or an alkoxy group having 1 to 18 carbon atoms (most preferably a methoxy group); $R^4$ represents a nitro group or an acylamino group preferably having 1 to 30 carbon atoms; and $R^5$ represents a hydrogen atom.

It is also particularly preferred that, when $R^1$ represents a 1-ethylcyclopropyl group, $R^3$ represents a halogen atom (most preferably a chlorine atom), $R^4$ represents an alkoxycarbonyl group preferably having 1 to 20 carbon atoms, and $R^5$ represents a halogen atom (most preferably a chlorine atom).

It is also particularly preferred that, when $R^1$ represents a p-methoxyphenyl group, $R^3$ represents a halogen atom (most preferably a chlorine atom), $R^4$ represents an alkoxycarbonyl group preferably having 1 to 20 carbon atoms, and $R^5$ represents a hydrogen atom.

It is also particularly preferred that, when $R^1$ represents an indoline-1-yl group, $R^3$ represents an alkoxy group having 1 to 18 carbon atoms (most preferably a dodecoxy group), $R^4$ represents a substituted or unsubstituted sulfamoyl group having 0 to 30 carbon atoms (most preferably an N-(o-chlorophenyl)sulfamoyl group), and $R^5$ represents a hydrogen atom.

The following combination is particularly preferred when $R^1$ represents a substituted anilino group in general formula (VII): $R^3$ represents a halogen atom (most preferably a chlorine atom); $R^4$ represents an alkoxycarbonyl group having 1 to 20 carbon atoms; and $R^5$ represents a hydrogen atom.

Second, the manufacturing methods are explained in detail.

A 1,3-dihalo-5,5-dimethylhydantoin used as a halogenating agent in the present invention can be easily obtained by halogenation of 5,5-dimethylhydantoin in an alkaline state, and it is a compound obtainable at a lower price than NBS and the like. Moreover, 5,5-dimethylhydantoin that is obtained after the above-mentioned halogenation is useful as a splitting-off group of the photographic yellow coupler. More specifically, 1,3-dichloro-5,5-dimethylhydantoin, 1-bromo-3-chloro-5,5-dimethylhydantoin, 3-bromo-1-chloro-5,5-dimethylhydantoin, and 1,3-dibromo-5,5-dimethylhydantoin are preferably used. Of these, particularly preferred compounds are 1,3-dichloro-5,5-dimethylhydantoin and 1,3-dibromo-5,5-dimethylhydantoin. Sometimes, two halogen atoms of these 1,3-dihalo-5,5-dimethylhydantoins effectively work for halogenation. As a result, 0.5 mol of the 1,3-dihalo-5,5-dimethylhydantoin is enough to obtain 1 mol of a 3-substituted-3-oxo-2-halopropionic acid amide compound, in many cases. The hydantoin compound is preferably used in an amount of 0.4 to 1.2 mol (most preferably 0.45 to 0.6 mol).

As a reaction solvent, use may be made of ester-type solvents, such as ethyl acetate; halogen-type solvents, such as methylene chloride; aromatic hydrocarbon-type solvents, such as benzene; amide-type solvents, such as N,N-dimethylacetamide and DMI; ketone-type solvents, such as acetone and methyl ethyl ketone; and an acetonitrile.

The reaction temperature is preferably from $-80°$ C. to $100°$ C., most preferably from $0°$ to $80°$ C.

A base may be added in order to improve reactivity of the active methylene group. When an electron-donating group (e.g. an amino group) exists on a benzene ring, sometimes bromination on the benzene ring preferentially occurs rather than the bromination of the active methylene group. In such case, the base is particularly effective. As the base, use may be made of inorganic bases and organic bases having respective pKa values (preferably the pKa values of 7 or higher) at which the active methylene group can dissociate. Examples of the base include sodium hydride, sodium methoxide, potassium carbonate, DBU, and triethylamine. These bases are preferably used in an amount of 0.5 to 3 equivalents, more preferably 0.9 to 2 equivalents, per 1 equivalent of the active methylene compound. When a base is used, the reaction temperature is generally from $-80°$ C. to $20°$ C., preferably from $-80°$ C. to $0°$ C.

Further, the 3-substituted-3-oxo-2-halopropionic acid amide compound thus obtained by halogenation, which has not been purified (i.e. contains 5,5-dimethylhydantoin as a secondary product), may be reacted with the 5,5-dimethylhydantoin in the presence of a base, to obtain a 3-substituted-3-oxo-2-(5,5-dimethylhydantoin-3-yl) propionic acid amide compound.

Examples of the base used in this method include sodium methoxide, sodium ethoxide, sodium carbonate, potassium carbonate, potassium tert-butoxide, and organic bases, such as triethylamine, DBU, and DBN.

As a reaction solvent, use may be made of ester-type solvents, such as ethyl acetate; halogen-type solvents, such as methylene chloride; aromatic hydrocarbon-type solvents, such as benzene and toluene; amide-type solvents, such as N,N-dimethylacetamide and DMI; ketone-type solvents, such as acetone; and an acetonitrile. Among them, the above organic solvents are preferably used, except the halogen-type solvents.

The reaction temperature is preferably from $-20°$ C. to $100°$ C., most preferably from $0°$ to $80°$ C.

A preferable amount of 5,5-dimethylhydantoin to be used is from 2 to 5 equivalents per 1 equivalent of the 3-substituted-3-oxo-2-halopropionic acid amide compound.

Specific examples of compounds represented by general formula (I) and compounds represented by general formula (II) are illustrated below. However, the present invention is not limited to these compounds.

TABLE 1 general formula (I)

| Compound | $R^1$ | n | $R^2$ | $X^1$ |
|---|---|---|---|---|
| (I)-1 | $(t)C_4H_9$ | 2 | 2-Cl-5-NHCOCHO, $C_2H_5$ / $C_5H_{11}(t)$ / $C_5H_{11}(t)$ | Br |

TABLE 1-continued general formula (I)

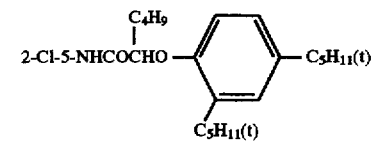

| Compound | $R^1$ | n | $R^2$ | $X^1$ |
|---|---|---|---|---|
| (I)-2 | (t)$C_4H_9$ | 2 | 2-Cl-5-NHCOC$_{15}$H$_{31}$ | Br |
| (I)-3 | (t)$C_4H_9$ | 2 | 2-Cl-5-NHCOC$_{17}$H$_{35}$ | Br |
| (I)-4 | (t)$C_4H_9$ | 2 | 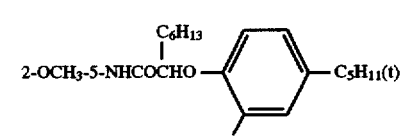 | Br |
| (I)-5 | (t)$C_4H_9$ | 2 | 2-Cl-5-CO$_2$C$_{12}$H$_{25}$ | Br |
| (I)-6 | (t)$C_4H_9$ | 2 | 2-OCH$_3$-5-NHCOC$_{17}$H$_{35}$ | Br |
| (I)-7 | (t)$C_4H_9$ | 2 | 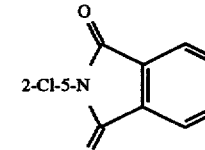 | Br |
| (I)-8 | (t)$C_4H_9$ | 2 | 2-Cl-5-NO$_2$ | Br |
| (I)-9 | (t)$C_4H_9$ | 2 | 2-Cl-5-NH$_2$ | Br |
| (I)-10 | (t)$C_4H_9$ | 2 | 2-OCH$_3$-5-NO$_2$ | Br |
| (I)-11 | (t)$C_4H_9$ | 2 | 2-OCH$_3$-5-NH$_2$ | Br |
| (I)-12 | (t)$C_4H_9$ | 2 | 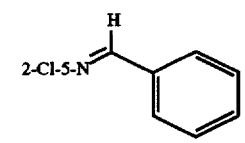 | Br |
| (I)-13 | (t)$C_4H_9$ | 2 | 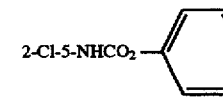 | Br |
| (I)-14 | (t)$C_4H_9$ | 2 | 2-Cl-5-NHCOCH$_3$ | Cl |
| (I)-15 | (t)$C_4H_9$ | 2 | 2-Cl-5-NHCOH | Br |
| (I)-16 | (t)$C_4H_9$ | 2 | 2-Cl-5-NHCO$_2$C$_4$H$_9^{(t)}$ | Br |
| (I)-17 | (t)$C_4H_9$ | 2 | 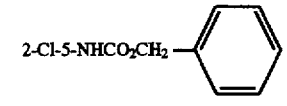 | Br |
| (I)-18 | (t)$C_4H_9$ | 2 | 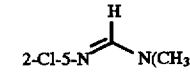 | Cl |
| (I)-19 | (t)$C_4H_9$ | 2 | 2-Cl-5-N=CH-N(CH$_3$)$_2$ | Br |
| (I)-20 | (t)$C_4H_9$ | 2 | 2-Cl-5-NHSO$_2$C$_{16}$H$_{33}$ | Cl |
| (I)-21 | (t)$C_4H_9$ | 2 | 2-OC$_4$H$_9$-5-NHSO$_2$C$_{16}$H$_{33}$ | Cl |
| (I)-22 | $C_2H_5$ (cyclopropyl) | 3 | 2-Cl-4-Cl-5-CO$_2$C$_{12}$H$_{25}$ | Br |

TABLE 1-continued
general formula (I)
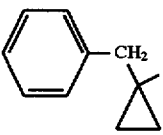
| Compound | R¹ | n | R² | X¹ |
|---|---|---|---|---|
| (I)-23 |  | 2 | 2-Cl-5-CO$_2$C$_{12}$H$_{25}$ | Br |
| (I)-24 | 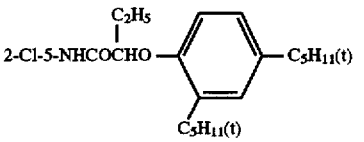 | 2 |  2-Cl-5-NHCOCHO— with C$_2$H$_5$, C$_5$H$_{11}$(t), C$_5$H$_{11}$(t) | Br |
| (I)-25 |  | 2 | 2-OCH$_3$-5-NHCOC$_{17}$H$_{35}$ | Cl |
| (I)-26 |  | 2 | 2-Cl-5-NHCOC$_{17}$H$_{35}$ | Br |
| (I)-27 |  | 2 | 2-Cl-5-NO$_2$ | Br |
| (I)-28 | 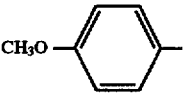 | 2 | 2-OCH$_3$-5-NO$_2$ | Br |
| (I)-29 | 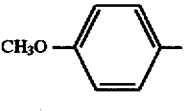 CH$_3$O— | 2 | 2-Cl-5-CO$_2$C$_{12}$H$_{25}$ | Br |
| (I)-30 | 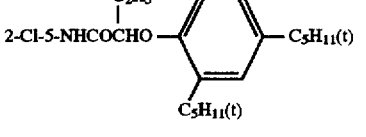 CH$_3$O— | 2 | 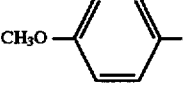 2-Cl-5-NHCOCHO— with C$_2$H$_5$, C$_5$H$_{11}$(t), C$_5$H$_{11}$(t) | Br |
| (I)-31 | CH$_3$O— | 2 | 2-Cl-5-NHCOC$_{17}$H$_{35}$ | Br |
| (I)-32 | CH$_3$O— | 2 | 2-Cl-5-NO$_2$ | Br |
| (I)-33 | CH$_3$O— | 2 | 2-Cl-5-NH$_2$ | Br |
| (I)-34 | C$_8$H$_{17}$O— | 2 | 2-Cl-5-NHSO$_2$C$_{16}$H$_{33}$ | Br |

TABLE 1-continued general formula (I)

$$R^1-\underset{\underset{X^1}{|}}{C}(=O)-CH-C(=O)-NH-C_6H_{3}(R^2)_n$$

| Compound | R¹ | n | R² | X¹ |
|---|---|---|---|---|
| (I)-35 | C₁₈H₃₇O–C₆H₄– | 2 | 2-OCH₃-5-OCH₃ | Cl |
| (I)-36 | 1-adamantyl | 2 | 2-Cl-5-CO₂C₁₂H₂₅ | Cl |
| (I)-37 | 1-adamantyl | 2 | 2-Cl-5-CO₂C₁₂H₂₅ | Br |
| (I)-38 | C₁₈H₃₇O–C₆H₄– | 3 | 2-Cl-4-Cl-5-CO₂C₁₂H₂₅ | Br |
| (I)-39 | C₁₈H₃₇O–C₆H₄– | 3 | 2-Cl-4-Cl-5-NHCOCH₃ | Br |
| (I)-40 | (t)C₄H₉ | 3 | 2-Cl-4-Cl-5-NHCOC₁₇H₃₅ | Br |
| (I)-41 | (t)C₄H₉ | 3 | 2-OCH₃-4-Cl-5-NHCOC₁₇H₃₅ | Br |
| (I)-42 | (t)C₄H₉ | 3 | 2-Cl-4-Cl-5-NHSO₂C₁₆H₃₃ | Br |
| (I)-43 | (t)C₄H₉ | 3 | 2-Cl-4-Cl-5-NHCOCH(C₂H₅)O–C₆H₃(C₅H₁₁(t))(C₅H₁₁(t)) | Br |
| (I)-44 | indolin-1-yl | 2 | 2-OC₁₈H₃₇-5-SO₂NH–C₆H₄-Cl | Br |
| (I)-45 | indolin-1-yl | 2 | 2-OC₁₈H₃₇-5-SO₂NH–C₆H₄-Cl | Cl |
| (I)-46 | indolin-1-yl | 2 | 2-Cl-5-SO₂NH–C₆H₃(Cl)(SO₂NHC₁₆H₃₃) | Br |

TABLE 1-continued general formula (I)

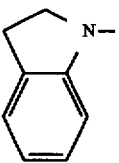

| Compound | R¹ | n | R² | X¹ |
|---|---|---|---|---|
| (I)-47 | 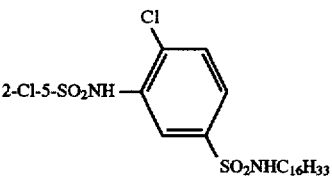 | 2 | 2-Cl-5-SO$_2$NH— (2-chloro-5-(hexadecylsulfamoyl)phenyl) | Cl |
| (I)-48 | 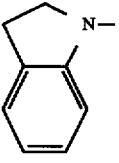 | 2 | 2-Cl-5-CO$_2$C$_{12}$H$_{25}$ | Br |
| (I)-49 | 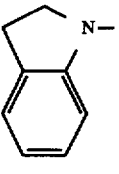 | 2 | 2-Cl-5-CO$_2$C$_{12}$H$_{25}$ | Cl |
| (I)-50 | 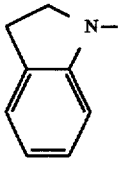 | 3 | 2-Cl-4-Cl-5-CO$_2$C$_{12}$H$_{25}$ | Br |
| (I)-51 | 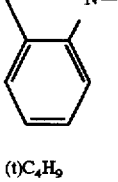 | 3 | 2-Cl-4-Cl-5-CO$_2$C$_{12}$H$_{25}$ | Cl |
| (I)-52 | (t)C$_4$H$_9$ | 2 | 2-Cl-5-NHCO—(CH$_2$)$_7$HC=CH(CH$_2$)$_7$CH$_3$ | Br |
| (I)-53 | (t)C$_4$H$_9$ | 2 | 2-Cl-5-NHCO—(CH$_2$)$_7$HC=CH(CH$_2$)$_7$CH$_3$ | Cl |
| (I)-54 | (t)C$_4$H$_9$ | 2 | 2-OCH$_3$-5-NHCO—(CH$_2$)$_7$HC=CH(CH$_2$)$_7$CH$_3$ | Br |
| (I)-55 | (t)C$_4$H$_9$ | 2 | 2-OCH$_3$-5-NHCO—(CH$_2$)$_7$HC=CH(CH$_2$)$_7$CH$_3$ | Cl |
| (I)-56 | 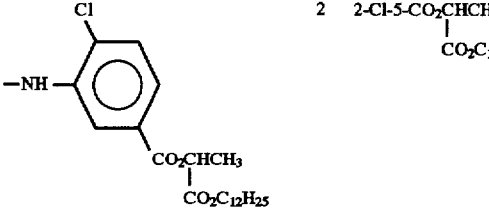 | 2 | 2-Cl-5-CO$_2$CHCH$_3$<br>\|<br>CO$_2$C$_{12}$H$_{25}$ | Cl |

TABLE 1-continued general formula (I)

| Compound | R¹ | n | R² | X¹ |
|---|---|---|---|---|
| (I)-57 | 4-Cl-C₆H₃(-NH-)(-CO₂CH(CH₃)CO₂C₁₂H₂₅-) | 2 | 2-Cl-5-CO₂CHCH₃ ($\vert$) CO₂C₁₂H₂₅ | Br |

TABLE 2 general formula (II)

| Compound | R¹ | n | R² |
|---|---|---|---|
| (II)-1 | (t)C₄H₉ | 2 | 2-Cl-5-NHCOCHO—[3,5-di-C₅H₁₁(t)-phenyl], CH with C₂H₅ |
| (II)-2 | (t)C₄H₉ | 2 | 2-Cl-5-NHCOC₁₅H₃₁ |
| (II)-3 | (t)C₄H₉ | 2 | 2-Cl-5-NHCOC₁₇H₃₅ |
| (II)-4 | (t)C₄H₉ | 2 | 2-Cl-5-NHCOCHO—[3,5-di-C₅H₁₁(t)-phenyl], CH with C₄H₉ |
| (II)-5 | (t)C₄H₉ | 2 | 2-Cl-5-CO₂C₁₂H₂₅ |
| (II)-6 | (t)C₄H₉ | 2 | 2-OCH₃-5-NHCOC₁₇H₃₅ |
| (II)-7 | (t)C₄H₉ | 2 | 2-OCH₃-5-NHCOCHO—[3,5-di-C₅H₁₁(t)-phenyl], CH with C₆H₁₃ |
| (I)-8 | (t)C₄H₉ | 2 | 2-Cl-5-NO₂ |
| (II)-9 | (t)C₄H₉ | 2 | 2-Cl-5-NH₂ |
| (II)-10 | (t)C₄H₉ | 2 | 2-OCH₃-5-NO₂ |
| (II)-11 | (t)C₄H₉ | 2 | 2-OCH₃-5-NH₂ |

TABLE 2-continued general formula (II)

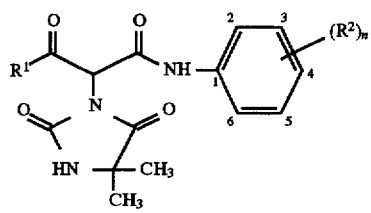

| Compound | R¹ | n | R² |
|---|---|---|---|
| (II)-12 | (t)C$_4$H$_9$ | 2 | 2-Cl-5-N(phthalimido) |
| (II)-13 | (t)C$_4$H$_9$ | 2 | 2-Cl-5-N=CH-C$_6$H$_5$ |
| (II)-14 | (t)C$_4$H$_9$ | 2 | 2-Cl-5-NHCOCH$_3$ |
| (II)-15 | (t)C$_4$H$_9$ | 2 | 2-Cl-5-NHCOH |
| (II)-16 | (t)C$_4$H$_9$ | 2 | 2-Cl-5-NHCO$_2$C$_4$H$_9$(t) |
| (II)-17 | (t)C$_4$H$_9$ | 2 | 2-Cl-5-NHCO$_2$-C$_6$H$_5$ |
| (II)-18 | (t)C$_4$H$_9$ | 2 | 2-Cl-5-NHCO$_2$CH$_2$-C$_6$H$_5$ |
| (II)-19 | (t)C$_4$H$_9$ | 2 | 2-Cl-5-N=CH-N(CH$_3$)$_2$ |
| (II)-20 | (t)C$_4$H$_9$ | 2 | 2-Cl-5-NHSO$_2$C$_{16}$H$_{33}$ |
| (II)-21 | (t)C$_4$H$_9$ | 2 | 2-OC$_4$H$_9$-5-NHSO$_2$C$_{16}$H$_{33}$ |
| (II)-22 | C$_2$H$_5$-(cyclopropyl) | 3 | 2-Cl-4-Cl-5-CO$_2$C$_{12}$H$_{25}$ |
| (II)-23 | C$_6$H$_5$CH$_2$-(cyclopropyl) | 2 | 2-Cl-5-CO$_2$C$_{12}$H$_{25}$ |
| (II)-24 | C$_2$H$_5$-(cyclopropyl) | 2 | 2-Cl-5-NHCOCH(C$_2$H$_5$)O-[2,4-di-C$_5$H$_{11}$(t)-C$_6$H$_3$] |
| (II)-25 | CH$_3$-(cyclopropyl) | 2 | 2-OCH$_3$-5-NHCOC$_{17}$H$_{35}$ |

TABLE 2-continued general formula (II)

[Structure: R¹-C(=O)-CH(N(-C(=O)-NH-Ar)(-C(=O)-C(CH₃)₂-NH-C(=O)H))-C(=O)-NH-Ar where Ar = phenyl with positions 1-6 and (R²)ₙ substituents]

| Compound | R¹ | n | R² |
|---|---|---|---|
| (II)-26 | C₂H₅-[cyclopropyl] | 2 | 2-Cl-5-NHCOC₁₇H₃₅ |
| (II)-27 | C₂H₅-[cyclopropyl] | 2 | 2-Cl-5-NO₂ |
| (II)-28 | C₂H₅-[cyclopropyl] | 2 | 2-OCH₃-5-NO₂ |
| (II)-29 | CH₃O-C₆H₄- | 2 | 2-Cl-5-CO₂C₁₂H₂₅ |
| (II)-30 | CH₃O-C₆H₄- | 2 | 2-Cl-5-NHCOCH(C₂H₅)O-[2,4-di-C₅H₁₁(t)-phenyl] |
| (II)-31 | CH₃O-C₆H₄- | 2 | 2-Cl-5-NHCOC₁₇H₃₅ |
| (II)-32 | CH₃O-C₆H₄- | 2 | 2-Cl-5-NO₂ |
| (II)-33 | CH₃O-C₆H₄- | 2 | 2-Cl-5-NH₂ |
| (II)-34 | C₁₈H₁₇O-C₆H₄- | 2 | 2-Cl-5-NHSO₂C₁₆H₃₃ |
| (II)-35 | C₁₈H₁₇O-C₆H₄- | 2 | 2-OCH₃-5-OCH₃ |
| (II)-36 | [indoline-N-yl] | 2 | 2-OC₁₈H₃₇-5-SO₂NH-[2-Cl-phenyl] |

TABLE 2-continued general formula (II)

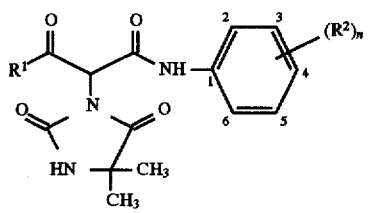

| Compound | R¹ | n | R² |
|---|---|---|---|
| (II)-37 | [indoline-N-] | 2 | 2-Cl-5-SO$_2$NH—[4-Cl-phenyl]-SO$_2$NHC$_{16}$H$_{33}$ |
| (II)-38 | [indoline-N-] | 2 | 2-Cl-5-CO$_2$C$_{12}$H$_{25}$ |
| (II)-39 | [indoline-N-] | 3 | 2-Cl-4-Cl-5-CO$_2$C$_{12}$H$_{25}$ |
| (II)-40 | (t)C$_4$H$_9$ | 2 | 2-Cl-5-NHCO—(CH$_2$)$_7$HC=CH(CH$_2$)$_7$CH$_3$ |
| (II)-41 | (t)C$_4$H$_9$ | 2 | 2-OCH$_3$-5-NHCO—(CH$_2$)$_7$HC=CH(CH$_2$)$_7$CH$_3$ |
| (II)-42 | [4-Cl-phenyl-NH-, with CO$_2$CHCH$_3$/CO$_2$C$_{12}$H$_{25}$] | 2 | 2-Cl-CO$_2$CHCH$_3$ \| CO$_2$C$_{12}$H$_{25}$ |

The 3-substituted-3-oxo-2-hydantoynylpropionic acid amide compound represented by formula (Y) is described below.

$R^{12}$, $R^{13}$, and $R^{14}$ each represent a hydrogen atom, or an alkyl group preferably having 1 to 18 carbon atoms.

$R^{15}$ represents an alkyl group having 3 or more carbon atoms (e.g. propyl, iso-propyl, n-butyl, iso-butyl, and n-hexyl).

$R^{16}$ and $R^{17}$ each represent a tertiary alkyl group having 4 or more carbon atoms (e.g. tert-butyl, tert-amyl, tert-octyl, and adamantyl).

Preferable compounds in formula (Y) are as follows:

(1) $R^{12}$ represents a hydrogen atom.

(2) $R^{13}$ and $R^{14}$ each represent a methyl group.

(3) $R^{15}$ represents an alkyl group having 3 to 18 carbon atoms.

(4) $R^{15}$ represents an alkyl group having 3 to 12 carbon atoms.

(5) $R^{15}$ represents an alkyl group having 4 to 6 carbon atoms.

(6) $R^{16}$ and $R^{17}$ each represent a tertiary alkyl group having 4 to 10 carbon atoms.

(7) $R^{16}$ and $R^{17}$ each represent a tert-butyl group or a tert-amyl group.

(8) $R^{16}$ and $R^{17}$ each represent a tertiary alkyl group having 5 to 8 carbon atoms.

(9) $R^{16}$ and $R^{17}$ each represent a tert-amyl group.

(10) The combination of one of (3) to (5) and one of (6) to (9) is more preferable.

(11) The combination of (1) and (2) is more preferable.

(12) The combination of (11) and (10) is more preferable.

(13) The combination of (11), (5), and (8) is more preferable.

(14) The combination of (11), (5), and (9) is more preferable.

Herein below are shown specific examples of the compound represented by formula (Y), but the present invention is not restricted to them.

TABLE 3 general formula (Y)

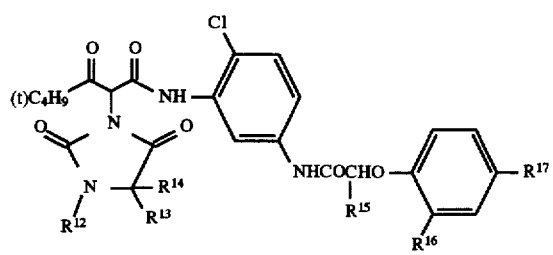

| Compound | $R^{12}$ | $R^{13}$ | $R^{14}$ | $R^{15}$ | $R^{16}$ | $R^{17}$ |
|---|---|---|---|---|---|---|
| (III)-1 | H | $CH_3$ | $CH_3$ | $C_3H_7$ | $(t)C_5H_{11}$ | $(t)C_5H_{11}$ |
| (III)-2 | H | $CH_3$ | $CH_3$ | $-CH(CH_3)_2$ | $(t)C_5H_{11}$ | $(t)C_5H_{11}$ |
| (III)-3 identical with (II)-4 | H | $CH_3$ | $CH_3$ | $-C_4H_9$ | $(t)C_5H_{11}$ | $(t)C_5H_{11}$ |
| (III)-4 | H | $CH_3$ | $CH_3$ | $-C_6H_{13}$ | $(t)C_5H_{11}$ | $(t)C_5H_{11}$ |
| (III)-5 | H | $CH_3$ | $CH_3$ | $-C_{10}H_{21}$ | $(t)C_5H_{11}$ | $(t)C_5H_{11}$ |
| (III)-6 | H | $CH_3$ | $CH_3$ | $-C_{12}H_{25}$ | $(t)C_5H_{11}$ | $(t)C_5H_{11}$ |
| (III)-7 | H | $CH_3$ | $CH_3$ | $C_4H_9$ | $(t)C_8H_{17}$ | $(t)C_8H_{17}$ |
| (III)-8 | H | $CH_3$ | $CH_3$ | $C_6H_{13}$ | $(t)C_8H_{17}$ | $(t)C_8H_{17}$ |
| (III)-9 | H | $CH_3$ | $CH_3$ | $C_4H_9$ | $(t)C_4H_9$ | $(t)C_4H_9$ |
| (III)-10 | H | $CH_3$ | $C_2H_5$ | $C_4H_9$ | $(t)C_5H_{11}$ | $(t)C_5H_{11}$ |
| (III)-11 | H | $CH_3$ | $C_2H_5$ | $C_6H_{13}$ | $(t)C_5H_{11}$ | $(t)C_5H_{11}$ |
| (III)-12 | H | $CH_3$ | $C_2H_5$ | $C_{10}H_{21}$ | $(t)C_5H_{11}$ | $(t)C_5H_{11}$ |
| (III)-13 | H | $C_2H_5$ | $C_2H_5$ | $C_3H_7$ | $(t)C_5H_{11}$ | $(t)C_5H_{11}$ |
| (III)-14 | H | $C_2H_5$ | $C_2H_5$ | $C_4H_9$ | $(t)C_5H_{11}$ | $(t)C_5H_{11}$ |
| (III)-15 | H | $C_2H_5$ | $C_2H_5$ | $C_6H_{13}$ | $(t)C_5H_{11}$ | $(t)C_5H_{11}$ |
| (III)-16 | $CH_3$ | $CH_3$ | $CH_3$ | $C_6H_{13}$ | $(t)C_5H_{11}$ | $(t)C_5H_{11}$ |
| (III)-17 | $C_8H_{17}$ | H | H | $C_6H_{13}$ | $(t)C_5H_{11}$ | $(t)C_5H_{11}$ |
| (III)-18 | $C_{12}H_{25}$ | H | H | $C_6H_{13}$ | $(t)C_5H_{11}$ | $(t)C_5H_{11}$ |

The hydantoin-substituted pivaloylacetic acid amide compound represented by formula (III) (i.e., a 3-substituted-3-oxo-2-hydantoinylpropionic acid amide compound) exhibits an excellent property as a photographic yellow coupler.

The compound represented by formula (Y) may be prepared by the manufacturing method of the present invention.

As the yellow coupler used in the present invention, one or more of the yellow couplers represented by formula (Y) may be used, which may be used in combination with other known yellow couplers.

The amount of the yellow coupler represented by formula (Y) of the present fourth invention (hereinafter referred to as the yellow coupler of the present invention) to be used in the silver halide color light-sensitive material of the present fifth invention (hereafter sometimes referred to simply as the light-sensitive material) is preferably in the range of 0.01 to 10 mmol/m², more preferably 0.05 to 5 mmol/m², and most preferably 0.1 to 2 mmol/m². Of course, two or more of the yellow couplers of formula (Y) may be used in combination, and couplers other than the couplers represented by formula (Y) can be additionally used.

It is sufficient that the light-sensitive material of the present invention has at least one layer containing the yellow coupler of the present invention on a base, and that the layer containing the yellow coupler of the present invention is a hydrophilic colloid layer on the base. Generally, the light-sensitive material can be composed of at least one blue-sensitive silver halide emulsion layer, at least one green-sensitive silver halide emulsion layer, and at least one red-sensitive silver halide emulsion layer, applied in the stated order onto the base, but some other order may be used. An infrared light-sensitive silver halide emulsion layer may take the place of at least one of the above-mentioned light-sensitive emulsion layers. These light-sensitive emulsion layers contain silver halide emulsions sensitive to respective wavelength regions and color couplers capable of forming dyes complementary to the lights to which they are sensitive, so that color reproduction may be effected by the subtractive color process. However, the constitution may be such that the light-sensitive emulsion layers and the hues formed by the color couplers may not have the above correspondence.

In the present invention, particularly preferably the yellow coupler of the present invention is used in the blue-sensitive silver halide emulsion layer.

The yellow coupler of the present invention can be introduced into the light-sensitive material by a variety of known dispersion methods, and preferably use is made of the oil-in-water dispersion method, wherein the yellow coupler is dissolved in a high-boiling organic solvent (if necessary, used in combination with a low-boiling organic solvent), the resulting solution is emulsified and dispersed in an aqueous gelatin solution, and then the emulsified dispersion is added to the silver halide emulsion.

As the silver halide emulsions, as well as other materials (e.g. additives) and the photographic constitutional layers (e.g. the arrangement of the layers) that are applied in the present invention, and as the processing methods and the processing additives that will be applied to the processing of the light-sensitive material, those described in JP-A Nos. 215272/1987 and 33144/1990 and European Patent EP No. 0,355,660A2 are preferably used.

Further, silver halide color photographic light-sensitive materials and processing methods thereof described, for example, in JP-A Nos. 34889/1993, 359249/1992, 313753/1992, 270344/1992, 66527/1993, 34548/1992, 145433/1992, 854/1990, 158431/1989, 90145/1990, 194539/1991, and 93641/1990, and in European Patent EP No. 0,520, 457A2, are also preferable.

As the silver halide used in the present invention, for example, silver chloride, silver bromide, silver chlorobromide, silver iodochlorobromide, and silver iodobromide can be used; but for quick processing, preferably use is made of a pure-silver chloride emulsion or a silver chlorobromide emulsion substantially free from silver iodide and having a silver chloride content of 90 mol % or more but 100 mol % or below, more preferably 95 mol % or more but 100 mol % or below, and particularly preferably 98 mol % or more but 100 mol % or below.

According to the present invention, a yellow coupler for use in silver halide color photographic materials and an intermediate thereof can be prepared simply and efficiently. The present invention can be applied to a compound having, in a molecule, a substituent that exerts a high reactivity to a halogenating agent or a mineral acid. Objective compounds can be synthesized under mild conditions. Further, yellow couplers economically and high in productivity can be provided.

EXAMPLE

The manufacturing methods of the present invention are explained in more detail in the following examples, however the present invention is not limited to these examples. In the descriptions of the following Examples, the compound mentioned as α-pivaloylacetic acid amide is identical to a 3-oxo-4,4-dimethylvaleric acid amide.

EXAMPLE 1

Synthesis of Compound (I)-1

Io 25 ml of ethyl acetate, was dispersed 5.71 g (0.01 mol) of N-[2-chloro-5-{2-(2,4-di-tert-amylphenoxy)butanoylamino}phenyl]-α-pivaloylacetic acid amide, which is easily obtained by a condensation reaction of 2-chloro-5-{2-(2,4-di-tert-amylphenoxy)butanoylamino}aniline with pivaloylacetic acid ester; and then to this was added, little by little, 1.57 g (0.0055 mol) of 1,3-dibromo-5,5-dimethylhydantoin, on an ice bath. After stirring for 1 hour, water was added to the resultant reaction mixture, followed by separation of solutions, and then a solvent was removed by fraction, to obtain on oily product. This product was subjected to silica gel column chromatography (n-hexane/ethyl acetate=10/1 to 5/1), for purification. As an oily product, 0.05 g of Compound (1)-1 was obtained.

Yield; 93%

$^1$H-NMR (200 MHz: CDCl$_3$): δ ppm 0.66 (t, 3H, J=7.3 Hz); 0.74 (t, 3H, J=7.3 Hz); 1.12 (t, 3H, J=6.7 Hz); 1.23 (s, 6H); 1.28 (s, 9H); 1.48 (s, 3H); 1.50 (s, 3H); 1.60 (m, 2H); 1.85–2.20 (m, 4H); 4.65 (t, 1H, J=6.0 Hz); 5.12 (s, 1H); 6.65 (d, 1H, J=8.0 Hz); 7.04 (dd, 1H, J=8.0, 2.7 Hz); 7.23 (d, 1H, J=2.7 Hz); 7.32 (d, 1H, J=8.7 Hz); 7.60 (dd, 1H, J=8.7, 2.7 Hz); 7.97 (s, 1H); 8.23 (d, 1H, J=2.7 Hz); 9.23 (s, 1H).

EXAMPLE 2

Synthesis of Compound (I)-8

In 10 ml of methylene chloride, was dissolved 2.9 g (0.01 mol) of N-(2-chloro-5-nitrophenyl)-α-pivaloylacetic acid amide, which is easily obtained by a reaction of 2-chloro-5-nitroaniline with pivaloylacetic acid ester; and then to this was added, slowly, 1.50 g (0.00525 mol) of 1,3-dibromo-5,5-dimethylhydantoin, on an ice bath, followed by stirring for 1 hour.

The post-processing was conducted in the similar manner as in Example 1, and the obtained oily product was crystallized by a mixed solvent of n-hexane/ethyl acetate and recrystallized, to obtain 3.59 g of Compound (I)-8 as a colorless crystal. Yield; 95%

Melting point; 138° to 140° C.

$^1$H-NMR (200 MHz: CDCl$_3$): δ ppm 1.34 (s, 9H); 5.20 (s, 1H); 7.60 (d, 1H, J=7.3 Hz); 7.97 (dd, 1H, J=7.3, 2.7 Hz); 9.26 (d, 1H, J=2.7 Hz); 9.48 (s, 1H);

EXAMPLE 3

Synthesis of Compound (II)-1 That Was Prepared Without Isolating Compound (I)-1 Synthesized According to the Method of Example 1

In 15 ml of methylene chloride, was dissolved 5.71 g (0.01 mol) of N-[2-chloro-5-{2-(2,4-di-tert-amylphenoxy)butanoylamino}phenyl]-α-pivaloylacetic acid amide, and then to this was added, little by little, 1.50 g (0.00525 mol) of 1,3-dibromo-5,5-dimethylhydantoin, on an ice bath. After stirring for 1 hour, the resultant suspension was dropped, on an ice bath, into a solution containing a sodium salt of 5,5-dimethylhydantoin previously prepared by adding 4.10 ml (0.02 mol) of 28% methanol solution of sodium methoxide to 10 ml of methylene chloride containing 3.20 g (0.025 mol) of 5,5-dimethylhydantoin. After stirring for another 1 hour, the reaction mixture was subjected to neutralization with dilute hydrochloric acid, separation of solutions, washing with water, and concentration, to obtain crude Compound (II)-1, as an oily product. This product was crystallized from ethanol, and 6.14 g of Compound (II)-1 was obtained.

Yield; 88%

Melting point; 95° to 98° C.

$^1$H-NMR (200 MHz: CDCl$_3$): δ ppm 0.67 (t, 3H, J=7.3 Hz); 0.75 (t, 3H, J=7.3 Hz); 1.11 (t, 3H, J=6.7 Hz); 1.22 (s, 6H); 1.28 (s, 9H); 1.48 (s, 3H); 1.50 (s, 3H); 1.60 (m, 2H); 1.9–2.15 (m, 4H); 4.64 (t, 1H, J=6.3 Hz); 5.62 (s, 1H); 6.00 (s, 1H); 6.66 (d, 1H, J=8.0 Hz); 7.05 (dd, 1H, J=8.0, 2.7 Hz); 7.22 (d, 1H, J=2.7 Hz); 7.30 (d, 1H, J=8.3 Hz ); 7.60 (dd, 1H, J=8.3, 2.7 Hz); 7.98 (s, 1H); 8.18 (d, 1H, J=2.7 Hz); 9.45 (s, 1H);

EXAMPLE 4

Synthesis of Compound (II)-8 That Was Prepared Without Separating Compound (I)-8 Synthesized According to the Method of Example 2

According to almost the same operation as in Example 2, an ethyl acetate solution of Compound (I)-8 was prepared, and this solution was dropped, on an ice bath, into a solution containing a sodium salt of 5,5-dimethylhydantoin previously prepared by adding 4.10 ml (0.02 mol) of 28% methanol solution of sodium methoxide to an ethyl acetate solution containing 3.20 g (0.025 mol) of 5,5-dimethylhydantoin. After stirring for another 1 hour, the reaction mixture was subjected to neutralization with dilute hydrochloric acid, separation of solutions, washing with water, and concentration. The product was crystallized from a mixed solvent of n-hexane/ethyl acetate, to obtain 3.61 g of Compound (II)-1, as a colorless crystal. Yield; 85%

Melting point; 205° to 208° C.

$^1$H-NMR (200 MHz: CDCl$_3$): δ ppm 1.30 (s, 9H); 1.54 (s, 3H); 1.58 (s, 3H); 5.67 (s, 1H); 6.05 (s, 1H); 7.56 (d, 1H, J=9.3 Hz); 7.95 (dd, 1H, J=9.3, 2.7 Hz); 9.25 (d, 1H, J=2.7 Hz); 10.00 (s, 1H).

EXAMPLE 5

Synthesis (1) of Compound (I)-9

In 10 ml of methylene chloride, was dissolved 2.69 g (0.01 mol) of N-(2-chloro-5-aminophenyl)-α-pivaloylacetic acid amide, and then to this was added 2.05 ml (0.01 mol) of 28% methanol solution of sodium methoxide. The inner temperature of the resultant solution was cooled to −5° C. with a coolant of ice/methanol. To this solution was added, little by little, 1.50 g (0.00525 mol) of 1,3-dibromo-5,5-dimethylhydantoin, while the temperature was kept at 0° C. or lower. After stirring for 2 hours, the product was subjected to neutralization with hydrochloric acid, extraction with ethyl acetate, washing with water, and concentration; and then silica gel column chromatography (n-hexane/ethyl acetate=2/1), for purification. As an oily product, 0.70 g of Compound (I)-9 was obtained.

Yield; 20%

$^1$H-NMR (200 MHz: CDCl$_3$)

Keto-enol equilibrium was observed as illustrated below. ((A) isomer and (B) isomer)

(A. isomer) δ ppm 1.30 (s, 9H); 3.58 (bs, 2H); 5.18 (s, 1H); 6.45 (dd, 1H, J=9.0, 2.7 Hz); 7.15 (d, 1H, J=9.0 Hz); 7.77 (d, 1H, J=2.7 Hz); 9.14 (s, 1H);

(B. isomer) δ ppm 1.30 (s, 9H); 3.58 (bs, 2H); 5.28 (s, 1H); 6.45 (dd, 1H, J=9.0, 2.7 Hz); 7.15 (d, 1H, J=9.0 Hz); 7.77 (d, 1H, J=2.7 Hz); 8.95 (s, 1H).

Under this reaction conditions, almost none of the product having an anilide ring substituted by a bromine atom, as obtained by the following Synthesis (2), was obtained; rather, purposively the active methylene group was exclusively brominated.

Synthesis (2) of Compound (II)-9

In 10 ml of methylene chloride, was dissolved 2.69 g (0.01 mol) of N-(2-chloro-5-aminophenyl)-α-pivaloylacetic acid amide, and then to this was added, little by little, 1.50 g (0.00525 mol) of 1,3-dibromo-5,5-dimethylhydantoin, on an ice bath. After stirring for 2 hours, the resultant solution was subjected to post-processing in the same way as Synthesis (1), to obtain 0.10 g of Compound (I)-9, as an oily product. Yield; 3%

Additionally, 1.28 g (yield 30%) of Compound 1 and 2.16 g (yield 62%) of Compound 2 were obtained. It is considered that, in the absence of a base, bromination of the aniline ring overwhelmingly occurs compared to bromination of the active methylene group.

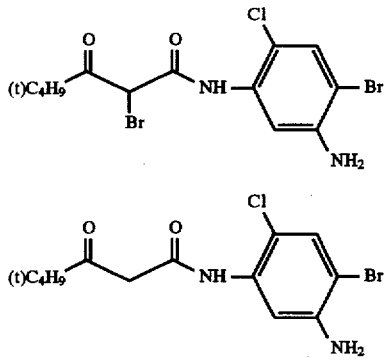

EXAMPLE 6

Synthesis of Compound (I)-22

Compound (I)-22 was obtained as an oily product by exactly the same reaction and processing as those of Example 2, except that N-(2,4-dichloro-5-dodecyloxycarbonylphenyl)-α-(1-ethylcyclopropylcarbonyl)acetic acid amide was used in place of N-(2-chloro-5-nitrophenyl)-α-pivaroylacetic acid amide.

$^1$H-NMR (200 MHz: CDCl$_3$): δ ppm 0.90 (t, 3H, J=6.7 Hz); 1.04 (t, 3H, J=7.3 Hz); 1.10 (m, 2H); 1.30–1.50 (m, 20H); 1.78 (m, 2H); 1.97 (m, 2H); 4.32 (t, 2H, J=6.7 Hz); 4.65 (s, 1H); 7.55 (s, 1H); 8.80 (s, 1H); 9.51 (s, 1H).

EXAMPLE 7

Synthesis of Compound (I)-29

Compound (I)-29 was obtained by exactly the same reaction and processing as those of Example 2, except that N-(2-chloro-5-dodecyloxycarbonylphenyl)-α-(p-methoxyphenylcarbonyl)acetic acid amide was used in place of N-(2-chloro-5-nitrophenyl)-α-pivaroylacetic acid amide.

Melting point; 96° to 98° C.

$^1$H-NMR (200 MHz: CDCl$_3$) δ ppm 0.88 (t, 3H, J=6.7 Hz); 1.26–1.32 (m, 18H); 1.75–1.81 (m, 2H); 3.93 (s, 3H); 4.32 (t, 2H, J=6.7 Hz); 5.69 (s, 1H); 7.01 (d, 2H, J=8.7 Hz); 7.50 (d, 1H, J=8.3 Hz); 7.79 (dd, 1H, J=8.3, 2.0 Hz); 8.07 (d, 2H, J=8.7 Hz); 8.98 (d, 1H, J=2.0 Hz); 9.68 (s, 1H).

EXAMPLE 8

Synthesis of Compound (II)-22

Compound (II)-22, as an oily product, was synthesized according to the method of Example 4.

$^1$H-NMR (200 MHz: CDCl$_3$): δ ppm 0.80 (m, 2H); 0.92 (t, 3H, J=6.7 Hz); 1.03 (t, 3H, J=7.3 Hz); 1.30 (m, 22H); 1.54 (s, 3H); 1.59 (s, 3H); 1.75 (m, 4H); 4.33 (t, 2H, J=6.7 Hz); 5.51 (s, 1H); 5.92 (s, 1H); 7.52 (s, 1H); 8.80 (s, 1H); 10.02 (s, 1H).

EXAMPLE 9

Synthesis of Compound (II)-29

Compound (I)-29 was synthesized according to Example 7, but, without isolation thereof, the resultant solution was subjected to a reaction with sodium salt of 5,5-dimethylhydantoin, followed by post-processing in the same way as Example 3, to obtain Compound (II)-29.

Melting point; 112° to 114° C.

$^1$H-NMR (200 MHz: CDCl$_3$): δ ppm 0.88 (t, 3H, J=7.0 Hz); 1.28 (m, 18H); 1.38 (s, 3H); 1.43 (s, 3H); 1.75 (m, 2H); 3.86 (s, 3H); 4.29 (t, 2H, J=7.0 Hz); 5.98 (s, 1H); 6.30 (s, 1H); 6.93 (d, 2H, J=9.0 Hz); 7.46 (d, 1H, J=9.0 Hz); 7.74 (dd, 1H, J=9.0, 2.0 Hz); 7.85 (d, 2H, J=9.0 Hz); 8.94 (d, 1H, J=2.0 Hz); 10.14 (s, 1H);

EXAMPLE 10

Synthesis of Compound (I)-44

In 50 ml of methylene chloride, 7.40 g (0.01 mol) of N-{2-octadecoxy-5-(2-chlorophenylsulfamoyl)phenyl}-α-indolinylcarbonylacetic acid amide, obtained according to the method described in JP-A No. 263249/1992, was dispersed, and 2.80 g (0.01 mol) of 1,3-dibromo-5,5-dimethylhydantoin was added thereto, followed by stirring at room temperature for 15 hours. The resultant solution was washed twice: first with 5% aqueous solution of sodium hydroxide, and then with water. After that, a solvent was removed by distillation from the solution. Crystallization was conducted with a mixed solvent of n-hexane/ethyl acetate. As a result, 7.53 g (yield; 92%) of Compound (I)-44 was obtained. Melting Point; 124° to 128° C.

EXAMPLE 11

Synthesis of Compound (I)-45

In 50 ml of ethyl acetate, was dispersed 7.40 g (0.01 mol) of N-{2-octadecoxy-5-(2-chlorophenylsulfamoyl)phenyl}-α-indolinylcarbonylacetic acid amide, obtained according to the method described in JP-A No. 263249/1992, and 2.0 g of 1,3-dichloro-5,5-dimethylhydantoin was added thereto, followed by stirring at room temperature for 15 hours. The resultant solution was washed twice: first with 5% aqueous solution of sodium hydride, and then with water. After that, a solvent was removed by distillation from the solution. Crystallization was conducted with a mixed solvent of n-hexane/ethyl acetate. As a result, 7.18 g (yield; 93%) of Compound (I)-45 was obtained. Melting Point; 78° to 80° C.

EXAMPLE 12

Synthesis of Compound (II)-40 using Compound (I)-52 as an intermediate

In 1 liter of acetonitrile, was dispersed 268.8 g (1 mol) of N-(2-chloro-5-aminophenyl)-α-pivaroylacetic acid amide, and then to this was added 81.5 ml (1.05 mol) of pyridine. After that, 30.0 g (1 mol) of oleyl chloride was dropped into the resultant solution at an internal temperature of 15° C. or lower, on an ice bath. Following stirring for 2 hours after the dropping, precipitated crystals were filtered. Next, 2 liters of ethyl acetate was added to the filtrate, followed by two washings with water. Acetonitrile was added to an oily product obtained by concentration, and precipitated crystals were filtered. As a total amount, 517.0 g of N-(2-chloro-5-oleoylaminophenyl)-α-pivaroylacetic acid amide was obtained, as a crystal. Yield; 97%

Next, 533.2 g (1 mol) of N-(2-chloro-5-oleoylaminophenyl)-α-pivaroylacetic acid amide was dispersed in 2 liters of methylene chloride, and then 150.1 g (0.525 mol) of 1,3-dibromo-5,5-dimethylhydantoin was added thereto at an internal temperature of 15° C. or below, on an ice bath, followed by stirring for 1 hour, to prepare a methylene chloride solution of Compound (I)-52.

Into this solution was dropped, at an internal temperature of 10° to 15° C., a methanol solution containing a sodium salt of 5,5-dimethylhydantoin previously prepared using 500 ml of methanol, 384.0 g (3 mol) of 5,5-dimethylhydantoin, and 410 ml (2 mol) of a 28% methanol solution containing sodium methoxide. Following stirring for 3 hours after the dropping, the resultant solution was washed with 5% aqueous solution of sodium hydroxide, to remove excess 5,5-dimethylhydantoin, followed by two washings with water. After that, a solvent was removed by distillation from the solution. Crystallization was conducted with acetonitrile, and 600.0 g (yield; 91%) of Compound (II)-40 was obtained, as a crystal. Melting Point; 129.5° to 131.5° C.

EXAMPLE 13

Synthesis of Compound (II)-36 That Is to be Synthesized Without Isolating Compound (I)-45 Synthesized According to the Method of Example 11

An ethyl acetate solution of Compound (I)-45 was prepared according to almost the same operation as that in Example 11, and it was dropped into a solution containing a sodium salt of 5,5-dimethylhydantoin previously prepared by adding 4.10 ml (0.02 mol) of a 28% methanol solution containing sodium methoxide to an ethyl acetate solution containing 3.20 g (0.025 mol) of 5,5-dimethylhydantoin. Next, the reaction mixture was heat-refluxed for 5 hours. The reaction solution was cooled to room temperature, and then subjected to neutralization with dilute hydrochloric acid, separation of solutions, washing with water, concentration, and recrystallization from a mixed solvent of n-hexane/ethyl acetate. As a result, 7.18 g of Compound (II)-36 was obtained, as a colorless crystal. Yield; 83% Melting Point; 146° to 148° C.

EXAMPLE 14

Synthesis of Exemplified Compounds (II-1), (III-1), (III-3), (III-4), and (III-9).

To produce a pivaloyl-type four-equivalent yellow coupler, several processes have been disclosed to date, and a process wherein a compound disclosed in European Patent No. 41,172, i.e., 5-amino-2-chloro-α-pivaloylacetoanilide (this compound is N-(2-chloro-5-aminophenyl)-3-oxo-4,4-dimethylvaleric acid amide by its other name), and a 1-alkyl-1-(2,4-di-t-pentylphenoxy)acetyl chloride are reacted by the two-phase Schotten-Baumann process (JP-A Nos. 110554/1991 and 110553/1991), is economically preferable as a process of synthesizing four-equivalent compounds corresponding to exemplified compounds (II-1), (III-1), (III-3), (III-4), and (III-9).

When the four-equivalent coupler obtained by this process is brominated with 1,3-dibromo-5,5-dimethylhydantoin (DMH-Br), a process wherein a solution in which the four-equivalent coupler is completely dissolved is added, dropwise, into a dispersion of the DMH-Br (the DMH-Br is not necessarily dissolved completely), is preferable because the process is simple. In this case, however, in view of the productivity, it is important that the solubility of the four-equivalent coupler in the solvent used be high. Since, in the two-phase Schotten-Baumann process for synthesizing a four-equivalent coupler, generally use is made of ethyl acetate or toluene as an organic solvent, the solubility of the four-equivalent coupler in ethyl acetate or toluene is important. Therefore, four-equivalent compounds corresponding to exemplified compounds (II-1), (III-1), (III-3), (III-4), and (III-9) were synthesized, and the solubility thereof in ethyl acetate and toluene was examined. The results thereof are shown in Table 4.

TABLE 4

[Structure: (t)C$_4$H$_9$-C(=O)-CH$_2$-C(=O)-NH-phenyl(Cl)-NHCOCHO(R$^{15}$)-phenyl(R$^{16}$)-R$^{17}$]

| | R$^{15}$ | R$^{16}$ and R$^{17}$ | Amount of solvent (ml) necessary to solve 1 g of four-equivalent products | |
|---|---|---|---|---|
| | | | Ethyl acetate | Toluene |
| Four-equivalent compound corresponding to exemplified compound (II-1) | C$_2$H$_5$ | t-C$_5$H$_{11}$ | 5.0 | 3.2 |
| Four-equivalent compound corresponding to exemplified compound (III-1) | n-C$_3$H$_7$ | t-C$_5$H$_{11}$ | 1.8 | 1.0 |
| Four-equivalent compound corresponding to exemplified compound (III-3) | n-C$_4$H$_9$ | t-C$_5$H$_{11}$ | 1.4 | 1.0 |
| Four-equivalent compound corresponding to exemplified Compound (III-4) | n-C$_6$H$_{13}$ | t-C$_5$H$_{11}$ | 0.8 | 0.8 |
| Four-equivalent compound corresponding to exemplified compound (III-9) | n-C$_4$H$_9$ | t-C$_4$H$_9$ | 9.0 | 8.0 |

As is shown in Table 4, it was found that, when R$^{16}$ and R$^{17}$ each were a t-pentyl group, the solubility in ethyl acetate or toluene of the four-equivalent compounds corresponding to exemplified compounds (III-1), (III-3), and (III-4), wherein R$^{15}$ had 3 or more carbon atoms, was 3 to 4 times higher than that of the four-equivalent compound corresponding to exemplified compound (II-1). It was also found that, when R$^{15}$ was a n-butyl group, the solubility of the four-equivalent compound corresponding to exemplified compound (III-3), wherein R$^{16}$ and R$^{17}$ each were a t-pentyl group, was 6 to 8 times higher than that of the four-equivalent compound corresponding to exemplified compound (III-9), wherein R$^{16}$ and R$^{17}$ each were a t-butyl group. For this reason, it can be said that the exemplified compounds (III-1), (III-3), and (III-4) are couplers excellent in productivity; that is, they are economically excellent couplers in comparison to the exemplified compounds (II-1) and (III-9) when the synthesis of four-equivalent products and the bromination to form two-equivalent products are carried out in the same solvent of ethyl acetate or toluene.

Further, there are two methods for taking out the coupler after the formation of the two-equivalent product: a crystallization method, and a method wherein the extract solution is concentrated completely and solidified and the solid is taken out (a whole amount takeout method). Where the two-equivalent product formation reaction proceeds approximately quantitatively, the latter method, i.e., the whole amount takeout method, is economically preferable because the product can be taken out without any loss. In this case, preferably the coupler is not crystallized, in view of the chemical engineering. Since the two-equivalent product formation of the exemplified compounds (II-1), (III-1), (III-3), (III-4), and (III-9) proceeds approximately quantitatively, the whole amount takeout method can be used. Therefore, after examining the crystallizability of these compounds, as is shown in Table 5, it was found that only the exemplified compound (II-1) crystallizes. Judging from this, it can be said that, in the whole amount takeout method, the exemplified compounds (III-1), (III-3), (III-4), and (III-9), wherein $R^{15}$ has 3 or more carbon atoms, are economically preferable couplers.

TABLE 5

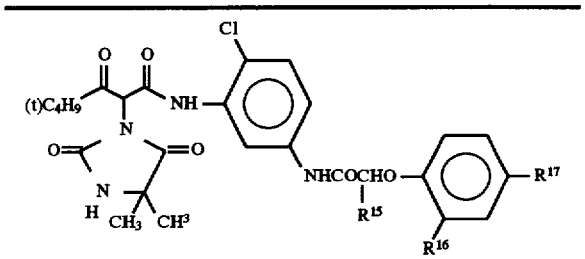

| Exemplified Compound No. | $R^{15}$ | $R^{16}$ and $R^{17}$ | Melting point (°C.) |
|---|---|---|---|
| (II)-1 | $C_2H_5$ | $t$-$C_5H_{11}$ | 95 to 98 (Ethanol) |
|  |  |  | 178 to 180 (EtOAc/n-hexane) |
| (III-1) | $n$-$C_3H_7$ | $t$-$C_5H_{11}$ | Amorphous (not crystallized) |
| (III-3) | $n$-$C_4H_9$ | $t$-$C_5H_{11}$ | Amorphous (not crystallized) |
| (III-4) | $n$-$C_6H_{13}$ | $t$-$C_5H_{11}$ | Amorphous (not crystallized) |
| (III-9) | $n$-$C_4H_9$ | $t$-$C_4H_9$ | Amorphous (not crystallized) |

The specific formulation of synthesizing couplers used in this Example is described in detail by taking the exemplified compound (III-3) as an example. Other exemplified compounds could be synthesized in approximately similar purities in a similar manner, except that the amounts of the solvent to be used were different because there was a difference in solubility of the four-equivalent couplers.

100 g of 5'-amino-2'-chloro-α-pivaloyl-acetoanilide was dissolved in 240 ml of toluene, and to the resulting solution was added a solution of 21.8 g of sodium carbonate in 200 ml of water. This mixture was stirred vigorously at room temperature, and 143.4 g of 2-(2,4-t-pentylphenoxy) hexanoyl chloride was added thereto, dropwise, over about 40 min. The dropping funnel was washed with 10 ml of toluene, which was added to the mixture, dropwise. After the addition, the mixture was stirred for about 2 hours, and then 6 ml of concentrated hydrochloric acid was added, to make the solution acidic. Then, the stirring was stopped, and after the mixture was allowed to stand for 5 min, the layers were separated, to obtain a toluene solution containing a four-equivalent compound corresponding to exemplified compound (III-3).

This toluene solution was added, dropwise, to a dispersion of 56.0 g of 1,3-dibromo-5,5-dimethylhydantoin (DMH-Br) in 100 ml of toluene at 15° C. or below. Thereafter, the mixture was stirred for about 30 min; then a methanol/toluene solution of 5,5-dimethylhydantoin-(DMH)-3-sodium salt (which was prepared by adding 143.6 g of a 28% sodium methoxide methanol solution to 105.2 g of DMH in 120 ml of toluene) was added, dropwise, thereto at 15° C. or below, and the mixture was stirred for about 2 hours. The mixture was washed with water; then 6 ml of concentrated hydrochloric acid and 400 ml of water were added thereto, to make it acidic, the layers were separated, and the toluene layer was washed with water twice. The toluene layer was concentrated under reduced pressure and was evaporated to dryness, and the resulting solid was triturated, to obtain, quantitatively, a powder of the exemplified compound (III-3) in the amorphous state. The obtained powder was analyzed by liquid chromatography (HPLC), and the purity was determined to be 97.5%.

EXAMPLE 15

Synthesis of Compound (I-8)

The same reaction and post-treatment as in Example 2 were repeated, except that, instead of methylene chloride as a solvent, acetone was used in the same amount, thereby obtaining Compound (I)-8, in a yield of 93%.

EXAMPLE 16

Synthesis of Compound (I)-1

The same reaction and post-treatment as in Example 1 were repeated, except that, instead of ethyl acetate as a solvent, toluene was used in the same amount, thereby obtaining Compound (I)-1, in a yield of 88%.

EXAMPLE 17

Synthesis of Compound (I)-44

The same reaction and post-treatment as in Example 10 were repeated, except that, instead of methylene chloride as a solvent, toluene was used in the same amount, thereby obtaining Compound (I)-44, in a yield of 82%.

EXAMPLE 18

Synthesis of Compound (I)-56

The process for the reaction and post-treatment according to those used in Example 11 was followed, except that use was made of 8.92 g (0.01 mol) of N,N'-{2-chloro-5-(1-dodecyloxycarbonyl)ethoxycarbonylphenyl}malonic acid diamide (which could be easily obtained by condensing dimethyl malonate with 2-chloro-5-(1-dodecyloxycarbonyl) ethoxycarbonylaniline), thereby obtaining 8.43 g (yield: 91%) of Compound (I)-56 in the amorphous state.

EXAMPLE 19

Synthesis of Compound (II)-57

The process for the reaction and post-treatment according to those used in Example 11 was followed, except that, instead of 1,3-dichloro-5,5-dimethylhydantoin, 1,3-dibromo-5,5-dimethylhydantoin in the same molar amount was used, thereby obtaining 7.48 g (yield: 77%) of Compound (I)-57 in the amorphous state.

EXAMPLE 20

Synthesis of Compound (II)-42 Which Is to Be Synthesized Without Isolating Compound (I)-56 Synthesized in Accordance with the Process in Example 18

The procedure similar to that of Example 18 was followed, to prepare a solution of Compound (I)-56. The solution was added, dropwise, to 5,5-dimethylhydantoin sodium salt, which was previously prepared by adding 4.10 ml (0.02 mol) of a sodium methoxide methanol solution (28%) to a solution of 3.2 g (0.025 mol) of 5,5-dimethylhydantoin in ethyl acetate, and the mixture was refluxed for 1 hour. The temperature of the mixture was brought to room temperature; dilute hydrochloric acid was added, to neutralize the mixture; the organic layer was separated, washed with water, and concentrated, and the concentrate was purified by silica gel column chromatography (n-hexane/ethyl acetate=3/1), thereby obtaining 8.67 g (yield: 85%) of Compound (II)-42 in the amorphous state.

EXAMPLE 21

Now, the solubilities of the couplers of the present invention in ethyl acetate are shown. The amounts of ethyl acetate required for dissolving 1 g of the couplers at 25° C. are shown in Table 6. It can be understood that, in comparison with Comparative Examples, the couplers of the present invention are quite excellent in solubility. It is quite unexpected that a difference of only one in the number of carbon atoms in a substituent makes the solubility extremely different.

TABLE 6

| Compound No. | $R^{15}$ | $R^{16}$ | $R^{17}$ | Amount of ethyl acetate (ml) necessary to solve 1 g of coupler | Remarks |
|---|---|---|---|---|---|
| (II)-1 | $C_2H_5$ | (t)$C_5H_{11}$ | (t)$C_5H_{11}$ | 8.0 | Comparative Example |
| (III)-1 | $C_3H_7$ | (t)$C_5H_{11}$ | (t)$C_5H_{11}$ | 1.0 | This Invention |
| (III)-3 | $C_4H_9$ | (t)$C_5H_{11}$ | (t)$C_5H_{11}$ | 0.9 | This Invention |

TABLE 6-continued

| Compound No. | $R^{15}$ | $R^{16}$ | $R^{17}$ | Amount of ethyl acetate (ml) necessary to solve 1 g of coupler | Remarks |
|---|---|---|---|---|---|
| (III)-4 | $C_6H_{13}$ | (t)$C_5H_{11}$ | (t)$C_5H_{11}$ | 0.7 | This Invention |
| (III)-9 | $C_4H_9$ | (t)$C_4H_9$ | (t)$C_4H_9$ | 1.0 | This Invention |

EXAMPLE 22

Preparation of Emulsified Dispersion 1

720 g of Comparative Coupler A, 120 g of Compound-1, 140 g of Compound-2, 40 g of Compound-3, 10 g of Compound-4, 130 ml of High-Boiling-Point Organic Solvent-1, 200 ml of High-Boiling-Point Organic Solvent-2, and 65 g of sodium dodecylbenzenesulfonate were weighed; then 900 ml of ethyl acetate was added thereto, and the mixture was heated to 60° C. and stirred, to dissolve the solids completely, followed by stirring at 50° C. for another 30 min. Separately from this, 650 g of gelatin, 0.3 g of Compound-5, and 9 g of calcium nitrate were weighed, and 2600 ml of water was added thereto, to dissolve them, at 50° C. The thus prepared two solutions were mixed and emulsified for 30 min by a stirring emulsifier at 5000 turns, to form a dispersion. Then water was added to the thus emulsified dispersion, to make it 10 kg, finally. The particle size of the emulsified dispersion was measured by the turbidity method, and it was found that the average particle diameter was 0.132 μm.

Comparative coupler A

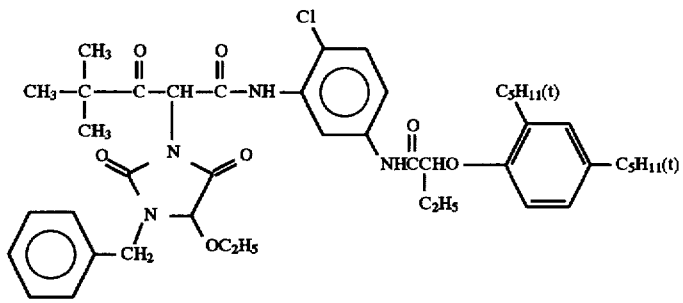

-continued
Compound-1
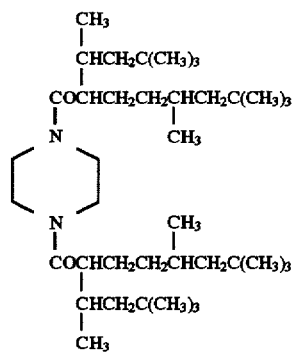
Compound-2
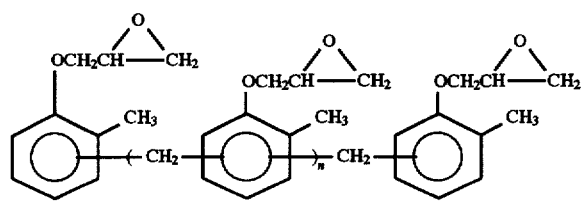
n = 7~8 (Average value)
Compound-3
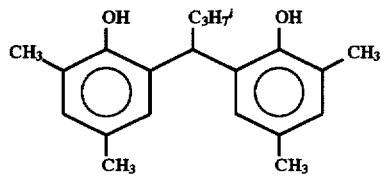
Compound-4
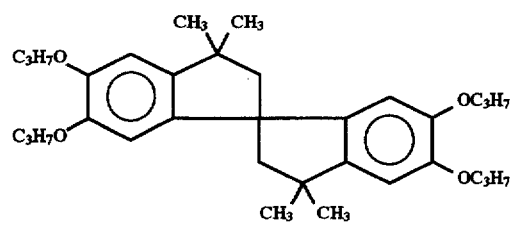
Compound-5
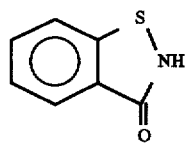
High-boiling-point organic solvent-1
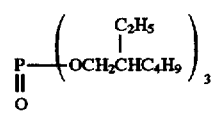

High-boiling-point organic solvent-2

-continued

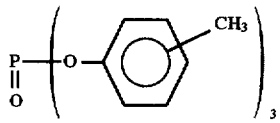

Preparation of Emulsified Dispersions 2 to 6

The procedure for Emulsified Dispersion 1 was repeated, except that Comparative Coupler A was replaced with the couplers shown in Table 7 in the same molar amount, thereby preparing Emulsified Dispersions 2 to 6. The particle size of these Emulsified Dispersions was measured in the same way as that used for Emulsified Dispersion 1.

Then, 2 kg of each of Emulsified Dispersions 1 to 6 was taken and was filtered through a filter having a cellulose filter with a pore size of 10 μm, and evaluation of the increase in filtration pressure and observation of the filtration residue were carried out.

Further, two 2-kg samples of each of Emulsified Dispersions 1 to 6 were taken, and after one was stored at 40° C. for 15 days and the other was stored at 5° C. for 40 days, in the same way as in the above the particle size was measured and the filtration pressure was evaluated, thereby evaluating the long-term stability of the Emulsified Dispersions.

The results are shown in Table 7.

particle size with the lapse of time is large, and an increase in filtration pressure is recognized. Particularly it was found that, when the emulsified dispersion of comparative coupler (II)-1 was stored at 40° C. for 15 days, a residue of crystals was observed on the filter and crystallization occurred, because of poor solubility of the coupler.

Thus, the couplers of the present invention are very excellent in solubility, and they are excellent in the property that they can form stable emulsified dispersions having a small particle size.

Further, a part of each of Samples 2 and 4 was coated, immidiately after preparation, on a paper support laminated with polyethylene and a part of each of Samples 2 and 4 was coated on a paper support laminated with polyethylene after it was stored at 5° C. for 40 days. Only on the surface of the support coated with the dispersion of Sample 2 stored at 5° C. for 40 days extraneous grains appeared throughout the surface, showing deterioration of the coated surface.

On the other hand, Sample 2 (just prepared or stored) and a silver chlorobromide emulsion A (comprising cubic silver

TABLE 7

| Sample No. | Coupler | Particle size | | | Filtration[1] pressure | | | Filtration[2] residue | | | Remarks |
|---|---|---|---|---|---|---|---|---|---|---|---|
| | | Fr | 5° C. | 40° C. | Fr | 5° C. | 40° C. | Fr | 5° C. | 40° C. | |
| 1 | A | 0.132 | 0.154 | 0.168 | ○ | Δ | Δ | ○ | ○ | ○ | Comparative Example |
| 2 | (II)-1 | 0.116 | 0.138 | 0.173 | ○ | Δ | x | ○ | ○ | x | Comparative Example |
| 3 | (III)-1 | 0.112 | 0.128 | 0.139 | ○ | ○ | ○ | ○ | ○ | ○ | This Invention |
| 4 | (III)-3 | 0.110 | 0.122 | 0.133 | ○ | ○ | ○ | ○ | ○ | ○ | This Invention |
| 5 | (III)-4 | 0.115 | 0.124 | 0.135 | ○ | ○ | ○ | ○ | ○ | ○ | This Invention |
| 6 | (III)-9 | 0.118 | 0.131 | 0.141 | ○ | ○ | ○ | ○ | ○ | ○ | This Invention |

Note:
Results of evaluation
1) Filtration pressure
  ○: No increase in filtration pressure was observed.
  Δ: Increase in filtration pressure was observed
  x: Filtration pressure increased remarkably, and filtration become inoperable.
2) Filtration residue
  ○: No residue on filter was observed.
  x: Residue on filter was observed.

As is apparent from Table 7, it can be understood that the couplers of the present invention can provide dispersions having small particle sizes, and the couplers are advantageous in view of color-forming properties. Further, the stability of the particle size is high and the change of the particle size with time is small. Further, the couplers of the present invention can provide stable emulsified dispersions that do not cause an increase in filtration pressure and crystallization with the lapse of time.

In contrast to that, it can be understood that Comparative Coupler A cannot provide a satisfactory small particle size, and it is disadvantageous in view of color-forming properties. Further, in Comparative Coupler (II)-1, the change in halide grains made up of a mixture of a large size emulsion A having an average grain size of 0.88 μm and a small size emulsion A having an average grain size of 0.70 μm in a molar ratio of 3:7 in terms of silver, wherein the deviation coefficients of the grain size distributions are 0.08 and 0.10 respectively; each of the emulsions has 0.3 mol % of silver bromide being localized on part of the surface of the grains; and the remaining part of grain is made of silver chloride) that had been prepared separately, were mixed together to give a coating solution. The coating solution was coated on a paper support laminated with polyethylene according to a usual manner, to produce a color photographic paper (101). Another color photographic paper (102) was obtained in the same manner as color photographic paper (101), except that corresponding Sample 4 was used in place of Sample 2. The color density for each of these color photographic papers 101 and 102 was measured. In color photographic paper 101 (Sample 2), the color density decreased by 0.4 in $D_{max}$ due to the storage at 5° C. for 40 days, while, in color photographic paper 102 (Sample 4), the color density did not decrease even after the storage.

Reference Example 1,3-dihalo-5,5-dimethylhydantoins are useful also in synthesizing 4-halo-1-naphthols that are synthetic intermediates of cyan couplers of color photographs, as shown below. These hydantoin compounds can be used in organic solvents (e.g., ethyl acetate, acetone, acetonitrile, toluene, and DMAc) other than halogen-type solvents and are industrially useful in a halogenation process wherein any halogen-type solvents are not used which are related to environmental problems. An example of the application of the compounds to the synthesis of a naphthol is illustrated below.

In 30 ml of acetone, 5.28 g (0.01 mol) of 2-(3-dodecoxypropylcarbamoyl)-5-isobutoxycarbonylamino-1-naphthol synthesized in accordance with the method described in JP-A No. 123158/1987 was dissolved and 2.00 g (0.01 mol) of 1,3-dichloro-5,5-dimethylhydantoin was added to the solution, followed by stirring for 2 hours at room temperature. Then 50 ml of ethyl acetate was added to the reaction mixture, followed by washing with a 5% aqueous sodium hydroxide solution and then washing with water. The solvent was distilled off and crystallization from acetonitrile was carried out, to give 5.17 g (yield: 92%) of 2-(3-dodecoxypropylcarbamoyl)-4-chloro-5-isobutoxycarbonylamino-1-naphthol.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of preparation, which comprises:
halogenating a 3-substituted-3-oxopropionic acid amide of formula (A):

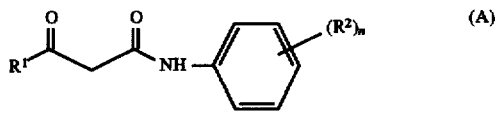

wherein $R^1$ represents an alkyl group, a cycloalkyl group, an aryl group, an amino group, or an indoline-1-yl group, $R^2$ represents a substituent that is suitable for a photographic yellow coupler, and n is an integer in the range of from 0 to 5 with the proviso that when n is 2 or greater, the substituents represented by $R^2$ are the same or different;
with a 1,3-dihalo-5,5-dimethylhydantoin to form a 3-substituted-3-oxo-2-halopropionic acid amide of formula (I):

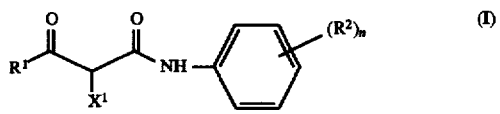

wherein $R^1$, $R^2$, and n are the same as in Formula (A) and $X^1$ represents a halogen atom.

2. The method as claimed in claim 1, wherein the 1,3-dihalo-5,5-dimethylhydantoin is 1,3-dibromo-5,5-dimethylhydantoin or 1,3-dichloro-5,5-dimethylhydantoin.

3. The method as claimed in claim 1, wherein $R^1$ represents a tert-butyl group, a 1-ethylcyclopropyl group, a p-methoxyphenyl group, or an indolin-1-yl group.

4. The method as claimed in claim 1, wherein $R^2$ represents a halogen atom, a cyano group, a nitro group, an amino group, a hydroxyl group, a carboxyl group, a sulfo group, an alkoxy group, an alkoxycarbonyl group, an acylamino group, a sulfonamide group, a carbamoyl group, a sulfamoyl group, an alkylsulfonyl group, an acyl group, an oxycarbonylamino group, or an imino group.

5. The method as claimed in claim 1, wherein $R^2$ represents a halogen atom, a nitro group, an amino group, an alkoxy group, an alkoxycarbonyl group, an acylamino group, or a sulfamoyl group.

6. The method as claimed in claim 1, wherein said halogenation step is carried out in the presence of a base.

7. The method as claimed in claim 1, which further comprises:
reacting said 3-substituted-3-oxo-2-halopropionic acid amide of formula (I) with 5,5-dimethylhydantoin in the presence of a base to form a 3-substituted-3-oxo-2-(5,5-dimethylhydantoin-3-yl)propionic acid amide of formula (II):

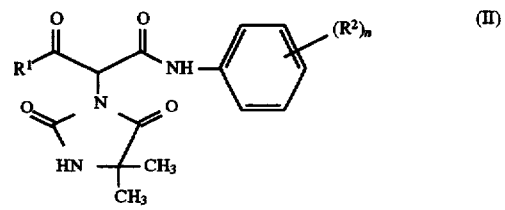

wherein $R^1$, $R^2$, and n are the same as in formula (A).

8. The method as claimed in claim 4, wherein n is an integer of from 1 to 5 and one $R^2$ substituent is 2-(2,4-di-tert-amylphenoxy)-butanoylamino.

9. The method as claimed in claim 1, wherein said 1,3-dihalo-5,5-dimethylhyantoin is used in an amount of from 0.45 to 0.6 mol per 1 mol of said amide of formula (A).

10. The method as claimed in claim 1, wherein said halogenation reaction is carried out at a temperature within the range of from 0° C. to 80° C.

11. The method as claimed in claim 1, wherein said halogenation reaction is carried out in the presence of a base and at a temperature from –80° C. to 0° C.

12. The method as claimed in claim 11, wherein said base is selected from the group consisting of sodium hydride, sodium methoxide, potassium carbonate, DBU, and triethylamine.

13. The method as claimed in claim 1, wherein said halogenation reaction is carried out in a solvent selected from the group consisting of esters, halogenated organic solvents, aromatics, amides, ketones, and acetonitrile.

14. The method as claimed in claim 13, wherein said solvent is selected from the group consisting of ethyl acetate, methylene chloride, benzene, N,N-dimethylacetamide, DMI, acetone, methyl ethyl ketone, and acetonitrile.

15. The method as claimed in claim 7, wherein said base is selected from the group consisting of sodium methoxide, sodium ethoxide, sodium carbonate, potassium carbonate, potassium tert-butoxide, triethylamine, DBU and DBN.

16. The method as claimed in claim 7, wherein said reaction of a compound of formula (I) with dimethylhydantoin is carried out at a temperature of from 0° C. to 80° C.

17. The method as claimed in claim 7, wherein said 5,5-dimethylhydantoin is used in an amount of from 2 to 5 equivalents per 1 equivalent of said compound of formula (I).

18. The method as claimed in claim 7, wherein the 1,3-dihalo-5,5-dimethylhydantoin is 1,3-dibromo-5,5-dimethylhydantoin or 1,3-dichloro-5,5-dimethylhydantoin.

19. The method as claimed in claim 7, wherein $R^1$ represents a tert-butyl group, a 1-ethylcyclopropyl group, a p-methoxyphenyl group, or an indolin-1-yl group.

20. The method as claimed in claim 7, wherein $R^2$ represents a halogen atom, a nitro group, an amino group, an alkoxy group, an alkoxycarbonyl group, an acylamino group, or a sulfamoyl group.

21. The method as claimed in claim 7, wherein the 3-substituted-3-oxo-2-halopropionic acid amide compound is reacted with 5,5-dimethylhydantoin in the presence of a base without purifying the 3-substituted-3-oxo-2-halopropionic acid amide compound after the halogenation step.

22. The method as claimed in claim 7, wherein the reaction of the 3-substituted-3-oxo-2-halopropionic acid amide compound with a 5,5-dimethylhydantoin is carried out in an organic solvent selected from the group consisting of ester-type solvents, aromatic hydrocarbon-type solvents, amide-type solvents, ketone-type solvents, and an acetonitrile.

23. A method of manufacturing a 3-substituted-3-oxo-2-(5,5-dimethylhydantoin-3-yl)propionic acid amide compound represented by general formula (II):

general formula (II)

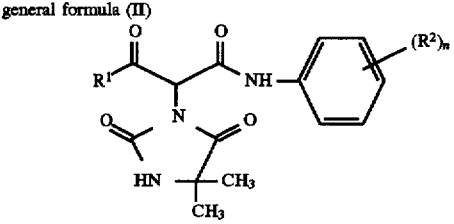

wherein $R^1$ represents an alkyl group, a cycloalkyl group, an aryl group, an amino group, or an indoline-1-yl group; $R^2$ represents a substituent that is suitable for a yellow coupler; and n represents an integer ranging from 0 to 5, with the proviso that when n is 2 or greater, the substituents represented by $R^2$ are the same or different, which comprises (1) halogenating a 3-substituted-3-oxopropionic acid amide compound with a 1,3-dihalo-5,5-dimethylhydantoin, to obtain a corresponding 3-substituted-3-oxo-2-halopropionic acid amid compound represented by general formula (I):

general formula (I)

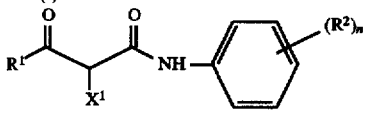

wherein $R^1$, $R^2$, and n each have the same meanings as those defined in general formula (II), and $X^1$ represents a halogen atom, and (2) reacting said 3-substituted-3-oxo-2-halopropionic acid amide compound in unpurified form with 5,5-dimethylhydantoin in the presence of a base to thereby form said compound of formula (II).

24. A 3-substituted-3-oxo-2-hydantoinylpropionic acid amide compound represented by general formula (Y):

general formula (Y)

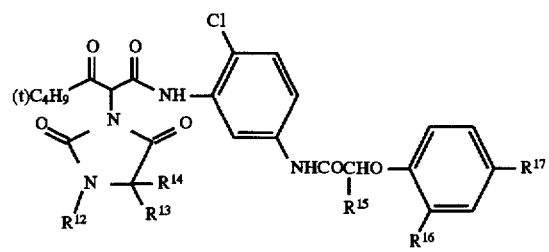

wherein $R^{12}$, $R^{13}$, and $R^{14}$ each represent a hydrogen atom or an alkyl group; $R^{15}$ represents an alkyl group having 3 or more carbon atoms; and $R^{16}$ and $R^{17}$ each represent a tertiary alkyl group having 4 or more carbon atoms.

25. The compound as claimed in claim 24, wherein $R^{12}$ represents a hydrogen atom; $R^{13}$ and $R^{14}$ each represent a methyl group; $R^{15}$ represents an alkyl group having 3 to 18 carbon atoms; and $R^{16}$ and $R^{17}$ each represent a tertiary alkyl group having 4 to 10 carbon atoms.

26. A photographic yellow coupler represented by general formula (Y):

general formula (Y)

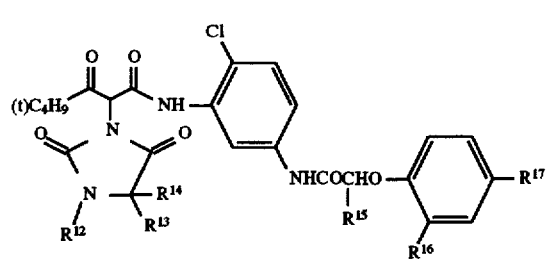

wherein $R^{12}$, $R^{13}$, and $R^{14}$ each represent a hydrogen atom or an alkyl group; $R^{15}$ represents an alkyl group having 3 or more carbon atoms; and $R^{16}$ and $R^{17}$ each represent a tertiary alkyl group having 4 or more carbon atoms.

27. The coupler as claimed in claim 26, wherein $R^{12}$ represents a hydrogen atom; $R^{13}$ and $R^{14}$ each represent a methyl group; $R^{15}$ represents an alkyl group having 3 to 18 carbon atoms; and $R^{16}$ and $R^{17}$ each represent a tertiary alkyl group having 4 to 10 carbon atoms.

* * * * *